US006594634B1

(12) United States Patent
Hampton et al.

(10) Patent No.: US 6,594,634 B1
(45) Date of Patent: Jul. 15, 2003

(54) METHOD AND APPARATUS FOR REPORTING EMERGENCY INCIDENTS

(75) Inventors: David R. Hampton, Woodinville, WA (US); Kathleen E. Briscoe, Carnation, WA (US); Robert E. Smith, Lynnwood, WA (US)

(73) Assignee: Medtronic Physio-Control Corp., Redmond, WA (US)

( * ) Notice: Subject to any disclaimer, the term of this patent is extended or adjusted under 35 U.S.C. 154(b) by 0 days.

(21) Appl. No.: 09/152,837

(22) Filed: Sep. 14, 1998

(51) Int. Cl.[7] ............................................. G06F 17/60
(52) U.S. Cl. ............................................. 705/3; 705/2
(58) Field of Search ..................... 705/2, 3, 9; 600/300; 704/243, 247; 707/6

(56) References Cited

U.S. PATENT DOCUMENTS

| 4,451,158 A | * | 5/1984 | Selwyn et al. ................. 368/63 |
| 4,588,383 A | * | 5/1986 | Parker et al. ................. 434/265 |
| 5,088,037 A | * | 2/1992 | Battaglia ..................... 600/300 |
| 5,101,424 A | * | 3/1992 | Clayton et al. ................ 379/10 |
| 5,327,341 A | * | 7/1994 | Whalen et al. ................. 705/3 |

(List continued on next page.)

FOREIGN PATENT DOCUMENTS

JP     7-141194 A   *  6/1995

OTHER PUBLICATIONS

Hennet, P.P. et al., "Event Record Generator," (Abstract only) IBM Technical Disclosure Bulletin, vol. 25, No. 11A, pp. 5578–5579, Apr. 1983.*

Meyer, R.H., "Principles of Airway Management," JAMA, the Journal of the American Medical Association, vol. 260, No. 15, p. 2305, Oct. 21, 1988.*

Anon., "Ensuring Effectiveness of Communitywide Cardiac Care," Journal of the American Medical Association, Oct. 28, 1992, vol. 16, p. 2289.*

Deich, W., "Parsley: A Command–Line Parser for Astronomical Applications," (Abstract only) Astronomical Society of the Pacific Conference Series, 1996, vol. 101, pp. 64–47.*

Primary Examiner—Nicholas David Rosen
(74) Attorney, Agent, or Firm—Shumaker & Sieffert, PA

(57) ABSTRACT

An event reporting program (48) is provided which electronically records information critical to reconstructing events occurring during an emergency incident. The event reporting program (48) includes an event recording component (204) for recording events as they occur during the incident, and a post-processing component (206) for further processing the events recorded by the event recording component after completion of the incident. The event recording component (204) enables an emergency service provider to input a plurality of event records (148) describing each event as it occurs and the time at which each event takes place. The event recording component also enables an emergency service provider to input a predefined protocol of expected event records. Each expected event record (148) identifies an event which is expected to occur during the incident and a time at which the event is expect to occur. Finally, the event recording component also includes a number of tools for providing and/or recording information in addition to the event records to the emergency service provider, e.g., an address book, drug guidelines, a narrative recorder, etc. The post-processing component (206), on the other hand, enables the user to modify or add to the event records (148) and other information previously recorded by the event recording component. In addition, the post-processing component (206) exports event records (148) to and imports event records (148) from external devices, such as a remote computer or medical electronic device. Finally, the post-processing component (206) generates a run report including the recorded event records (148) and information related to the incident.

40 Claims, 25 Drawing Sheets

U.S. PATENT DOCUMENTS

| | | | | | |
|---|---|---|---|---|---|
| 5,592,945 | A | * | 1/1997 | Fiedler | 600/523 |
| 5,634,100 | A | * | 5/1997 | Capps | 705/9 |
| 5,664,109 | A | * | 9/1997 | Johnson et al. | 705/2 |
| 5,668,954 | A | * | 9/1997 | Feder et al. | 369/30.24 |
| 5,683,423 | A | * | 11/1997 | Post | 607/5 |
| 5,725,472 | A | * | 3/1998 | Weathers | 600/21 |
| 5,732,221 | A | * | 3/1998 | Feldon et al. | 705/3 |
| 5,823,948 | A | * | 10/1998 | Ross, Jr. et al. | 600/300 |
| 5,924,074 | A | * | 7/1999 | Evans | 705/3 |
| 5,954,641 | A | * | 9/1999 | Kehr et al. | 600/300 |
| 6,000,828 | A | * | 12/1999 | Leet | 705/2 |
| 6,026,363 | A | * | 2/2000 | Shepard | 705/3 |
| 6,031,526 | A | * | 2/2000 | Shipp | 345/302 |
| 6,047,259 | A | * | 4/2000 | Campbell et al. | 705/3 |
| 6,055,494 | A | * | 4/2000 | Friedman | 704/9 |
| 6,076,065 | A | * | 6/2000 | Clawson | 705/2 |
| 6,078,894 | A | * | 6/2000 | Clawson et al. | 705/11 |
| 6,085,493 | A | * | 7/2000 | DeBusk et al. | 53/445 |
| 6,090,045 | A | * | 7/2000 | Leahy et al. | 600/301 |
| 6,117,073 | A | * | 9/2000 | Jones et al. | 600/300 |
| 6,125,350 | A | * | 9/2000 | Dirbas | 705/2 |
| 6,148,297 | A | * | 11/2000 | Swor et al. | 707/3 |
| 6,208,996 | B1 | * | 3/2001 | Ben-Shachar et al. | 707/104 |
| 6,401,118 | B1 | * | 6/2002 | Thomas | 709/224 |
| 6,434,531 | B1 | * | 8/2002 | Lancelot et al. | 705/3 |
| 6,442,295 | B2 | * | 8/2002 | Navoni et al. | 382/229 |
| 6,457,004 | B1 | * | 9/2002 | Nishioka et al. | 707/5 |
| 2002/0100052 | A1 | * | 7/2002 | Daniels | 725/87 |

* cited by examiner

Event Recorder

Incident ID 081198-1047   Provider ID Bsmith   Start: 08/11/98 10:49:30

Protocol
ABC

Event
_____ (Systolic) / _____ (Diastolic)

| Event Time 68a | Expected 68b | Event 68c | Detail 68d |
|---|---|---|---|
| Chronicle | 10:49 | Arrive Patient | |
| 10:50 | 10:59 | BP | 110/60 |
| | 11:00 | CPR | |
| | 11:01 | Monitor | |
| | 11:02 | Shock | 200 J |
| | 11:03 | Shock | 200 to 300 J |
| | 11:04 | Shock | 360 J |
| | 11:04 | Resp Rate | |
| | | Pulse | |

Current: 10:51:27 AM
Elapsed: 00:01:57

End Incident

*Fig. 6H.*

Event Recorder

Incident ID 081198-1047

Protocol ABC

Current: 10:52:21 AM
Elapsed: 00:02:51

[End Incident]

Drug Guidelines

Albuterol

Proventil, Ventolin

Indications:
Treatment of bronchospasm from emphysema or asthma. Prevention of exercise-induced bronchospasm.

Contraindications and Interactions:
Use with caution in patients with diabetes, hyperthyroidism, and cerebrovascular disease.

Additional Information:
Antagonized by beta-blockers (I.e.: Inderal, Lopressor)

Adult Dose:
2.5 mg: dilute 0.5 ml of the 0.5% solution for inhalation with 2.5 ml normal saline in nebulizer over 10-15 minutes. 2 inhalations with metered-dose inhaler every 4-6 hours.

Pediatric Dose:
1.0 mg: dilute 0.5 ml of 0.5% solution for inhalation.

[Dose]

Post Event Things

Incident ID  081198-1047    Provider ID  Bsmith    Start:  8/11/98 10:49:30 AM

Chronicle

| Event | Expected | Event | Detail | Source |
|---|---|---|---|---|
| 10:41 | | Call 911 | | CAD |
| 10:43 | | Unit Dispatched | A-51, Smith, Jones, Bel | CAD |
| 10:45 | | Unit Mobile | | CAD |
| 10:48 | | Arrive Scene | | CAD |
| | 10:49 | Arrive Patient | | Bsmith |
| 10:50 | 10:59 | BP | 110/60 | Bsmith |
| 11:00 | | CPR | | Bsmith |
| | 11:00 | Depart Scene | | CAD |
| | 11:01 | Monitor | | Bsmith |
| | 11:02 | Shock | 200 J | Bsmith |
| | 11:03 | Shock | 200 to 300 J | Bsmith |
| | 11:04 | Shock | 360 J | Bsmith |
| | 11:04 | Pulse | | Bsmith |
| | 11:04 | Resp Rate | | Bsmith |
| | | BP | | Bsmith |

- Device Events
- CAD Events
- Narrative Data
- Addt'l Data
- Narrative Edit
- Run Report
- Export Data
- New Case
- Exit Back

Fig. 8C.

Post Event Things

Incident ID 081198-1047   Provider ID Bsmith   Start: 8/11/98 10:49:30 AM

Back

Chronicle

| Event | Expected | Event | Detail | Source |
|---|---|---|---|---|
| 10:41 | | Call 911 | | CAD |
| 10:43 | | Unit Dispatched | A-51, Smith, Jones, Bel | CAD |
| 10:45 | | Unit Mobile | | CAD |
| 10:48 | 10:49 | Arrive Scene | | Bsmith |
| 10:50 | | Arrive Patient | | Bsmith |
| 10:53 | | BP | 110/60 | Bsmith |
| 10:53 | | RecdECG | #1 | LP12 |
| | | Heart Rate | 92 | LP12 |
| | 10:59 | CPR | | Bsmith |
| 11:00 | | Depart Scene | | CAD |
| | 11:00 | Monitor | | Bsmith |
| | 11:01 | Shock | 200 J | Bsmith |
| | 11:02 | Shock | 200 to 300 J | Bsmith |
| | 11:03 | Shock | 360 J | Bsmith |
| | 11:04 | Resp Rate | | Bsmith |

Device Events
CAD Events
Narrative Data
Addt'l Data
Narrative Edit

Run Report
Export Data
New Case
Exit

METHOD AND APPARATUS FOR REPORTING EMERGENCY INCIDENTS

FIELD OF THE INVENTION

This invention generally relates to a method and apparatus for allowing a trained emergency service provider to report emergency incidents and, more specifically, a method and apparatus for allowing an emergency service provider to electronically collect and record information regarding an emergency incident and generate a meaningful report of such data.

BACKGROUND OF THE INVENTION

Emergency care is commonly delivered to a patient at the scene of an incident by trained emergency service providers such as paramedics, police officers, emergency medical technicians (EMTs), etc. These providers work within a community-based Emergency Medical System (EMS) under the supervision of a medical director who establishes operating protocols, oversees training, and monitors the system's effectiveness. System effectiveness is assessed primarily by evaluating patient outcomes, often through secondary measures that are closely associated with long-term survival such as response time, protocol adherence, and time to delivery of effective therapy. Typically, such information is recorded manually by the emergency service provider in a paper run report including a patient information portion for recording personal patient data, a narrative portion for recording the emergency service provider's clinical narrative, and an event log portion for recording each of the treatment events that take place during the incident and their associated times of occurrence. Consequently, the report captures the time interval for the EMS to respond to the call for help, the patient's presenting signs and symptoms, the delay until therapy is applied, etc. The run report can then be later used to produce statistical summaries of overall EMS response characteristics. One example of a statistical analysis report based on a run report is the Utstein Style report for measuring response effectiveness in cases where the patient has suffered cardiac arrest.

In order to generate incident run reports and statistical summaries such as the ones specified by the Utstein Style, raw event data must reliably collected, coded, and entered into a database. Often, the sources of raw event data are widely dispersed. Dispatch event information is provided by a Computer-Aided Dispatch (CAD) system, while vital signs and therapeutic information events are found in medical devices used on-scene during patient treatment. Emergency service provider narratives are often written into run reports produced after the incident is concluded. It is difficult for any EMS system to collate these disparate pieces of information into a single database. Often the sequence of events and their exact times can only be approximated from the records. The event log recorded in the run report can be especially inaccurate, since it is often compiled after-the-fact, perhaps days later, from memory and written notes. Efforts to introduce electronic versions of paper run reports for on-scene event capture have not been successful because the equipment is bulky and expensive, its use interferes with patient care, and the menu-driven database interface fails to capture the full range of essential events needed. A particular failing is that the accurate event times are not recorded along with the events themselves, making calculation of response intervals inaccurate.

In order to more accurately record information critical to reconstructing incident events accurately, a more versatile, focused approach to electronic data collection for run reports is needed. The approach should provide for recordation of simple background information, such as the patient's name and the incident location, as well as a summary of each event that occurred during the emergency incident and the particular time of the event. To be useful, the associated time should be accurate to within one minute. Finally, the approach should provide for capture of a clinical narrative by the emergency service provider which is the provider's account of the incident, including the provider's subjective appraisal, objective findings, and the assessments performed, and the provider's planned therapies and procedures. The approach should collect all of this information, and merge the information with CAD and medical device data to populate the database needed for incident reporting and assessment of system effectiveness.

SUMMARY OF THE INVENTION

The present invention provides a computer-readable medium having computer-executable components for recording and reporting an emergency incident comprising a plurality of events associated with treatment of a patient during the incident. The computer executable components include an event recording component and a post-processing component. The event recording component records events as they occur during the incident, while the post-processing component further processes the events recorded by the event recording component once the incident has concluded.

The event recording component records events by enabling a emergency service provider to input a plurality of event records, wherein each event record identifies an event which occurred during the incident and a time at which the event occurred. The event recording component also records events input by the emergency service provider as a predefined treatment protocol for the patient, wherein the predefined treatment protocol comprises a plurality of predefined event records and wherein each predefined event record identifies an event which is expected to occur during the incident and a time at which the event is expected to occur during the incident. Finally, the event recording component includes at least one subcomponent for providing information regarding the incident in addition to the event records recorded by the event recording component. The subcomponent may be an address book component, a drug guideline component, a medication identification component, a narrative story component, a stop watch component or a drug dosage/infusion component.

The post-processing component, on the other hand, enables the user to modify the event records previously recorded by the event recording component, as well as record additional information regarding the incident. In addition, the post-processing component incorporates event records recorded by an external source, such as a remote computer or medical electronic device, with the event records previously recorded by the event recording component. The post-processing component also exports event records to external devices, such as a remote computer, for further processing and record-keeping. Finally, the post-processing component generates a run report containing event records and related information recorded and processed by the event recording component and the post-processing component.

In accordance with yet other aspects of the present invention, the event recording component and the post-processing component enable the user to verbally input event records and related information.

A method and apparatus capable of performing actions generally consistent with the event recording component and the post-processing component described above represent further aspects of the present invention.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIGS. 6A–6L are various windows produced by the event reporting program for recording events and related information during the emergency incident;

FIGS. 8A–8F are various windows produced by the event reporting program for further processing events and related information after the occurrence of the emergency incident.

DETAILED DESCRIPTION OF THE PREFERRED EMBODIMENT

Figure 1:
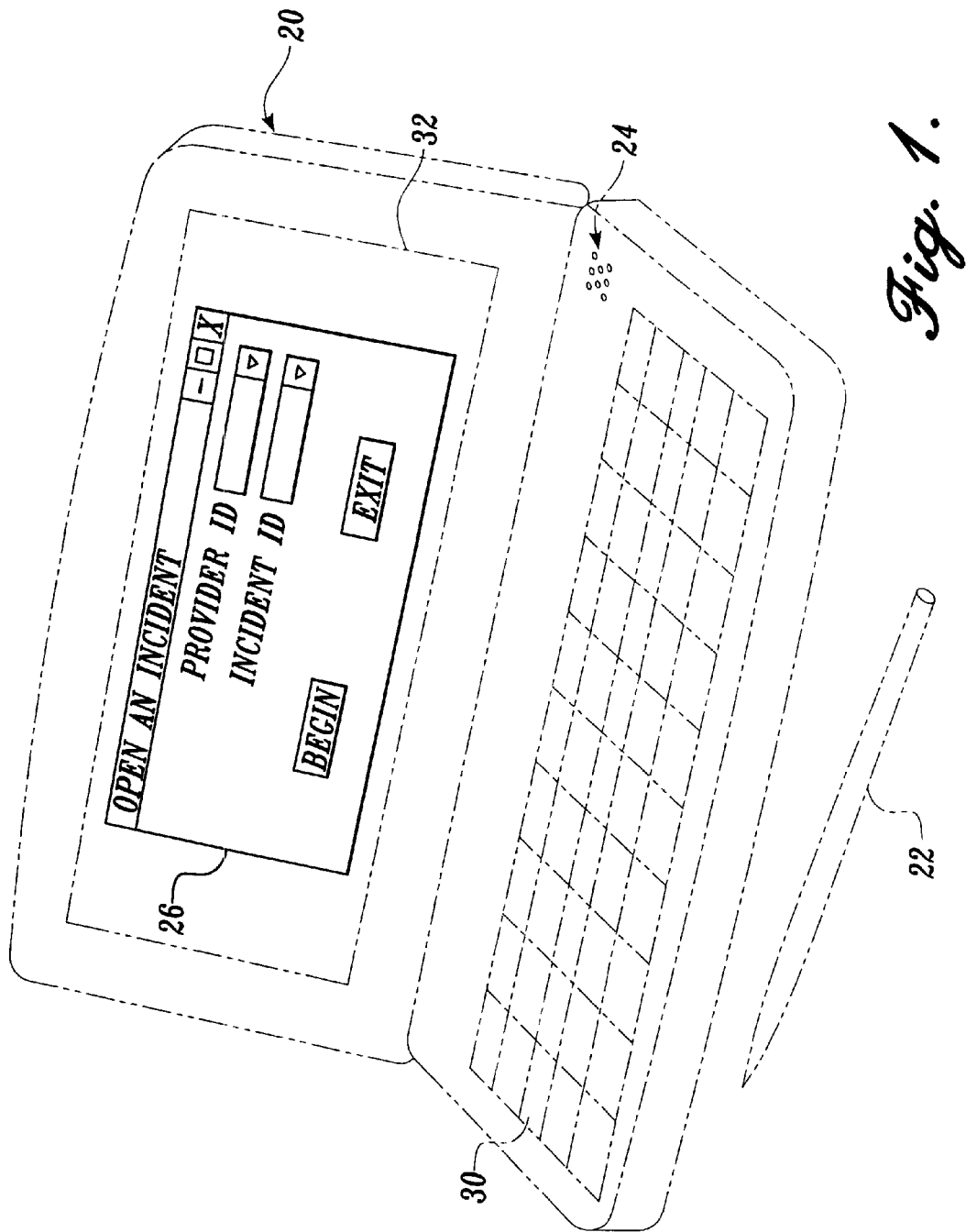
FIG. 1 is an isometric view of a hand-held computer that is installed with an event reporting program formed in accordance with the present invention to record and report an emergency incident.

FIG. 1 illustrates a hand-held computer 20 used to record and report emergency incidents in accordance with the present invention. More specifically, the hand-held computer 20 shown in FIG. 1 is installed with an event reporting program 48 formed in accordance with the present invention to electronically record and report emergency incidents. The hand-held computer 20 comprises a touch screen display 32 for displaying the windows produced by the event recording program 48 of the present invention to prompt an emergency service provider to record events and related information that occur during an emergency incident. In order to record information and events, the emergency service provider selects options provided by the displayed windows using a touch screen pen 22. In addition, the emergency service provider may record information and events using a keyboard 30. In yet other embodiments of the present invention, the hand-held computer 20 includes a speaker/microphone 24 and appropriate voice recognition software for recognizing voice commands and recording the voice input of events and information. Those of ordinary skill in the art will appreciate that such voice recognition software is readily available off-the-shelf and can be installed on the hand-held computer in addition to the event reporting program 48. Further, the hand-held computer 20 may be equipped with a high quality digital data recorder and a noise canceling microphone in order to allow for better usage of the event reporting program in typically noisy and turbulent EMS field situations. Consequently, the emergency service provider can control the event reporting program 48 and record events and related information merely by speaking, rather than using a more traditional user input device such as a mouse, keypad, or touch screen/pen, etc. As a result, the emergency service provider has the free use of his or her hands to treat the patient at all times and need not interrupt treatment to operate the event reporting program 48.

Those of ordinary skill in the art will recognize that although a hand-held computer 20 is depicted in FIG. 1, the event reporting software program 48 of the present invention can be installed and implemented on any type of portable data entry system, including but not limited to, a laptop computer, a personal device assistant, or even a medical electronic device such as a defibrillator. In addition, the portable data entry system may implement any type of user input device such as a mouse, keypad, touch screen, microphone, wireless headset, etc. to input events and related incident information. In yet other embodiments, the event reporting program 48 may be installed on a more stationary computer system, such as a personal computer or workstation.

Figure 2:
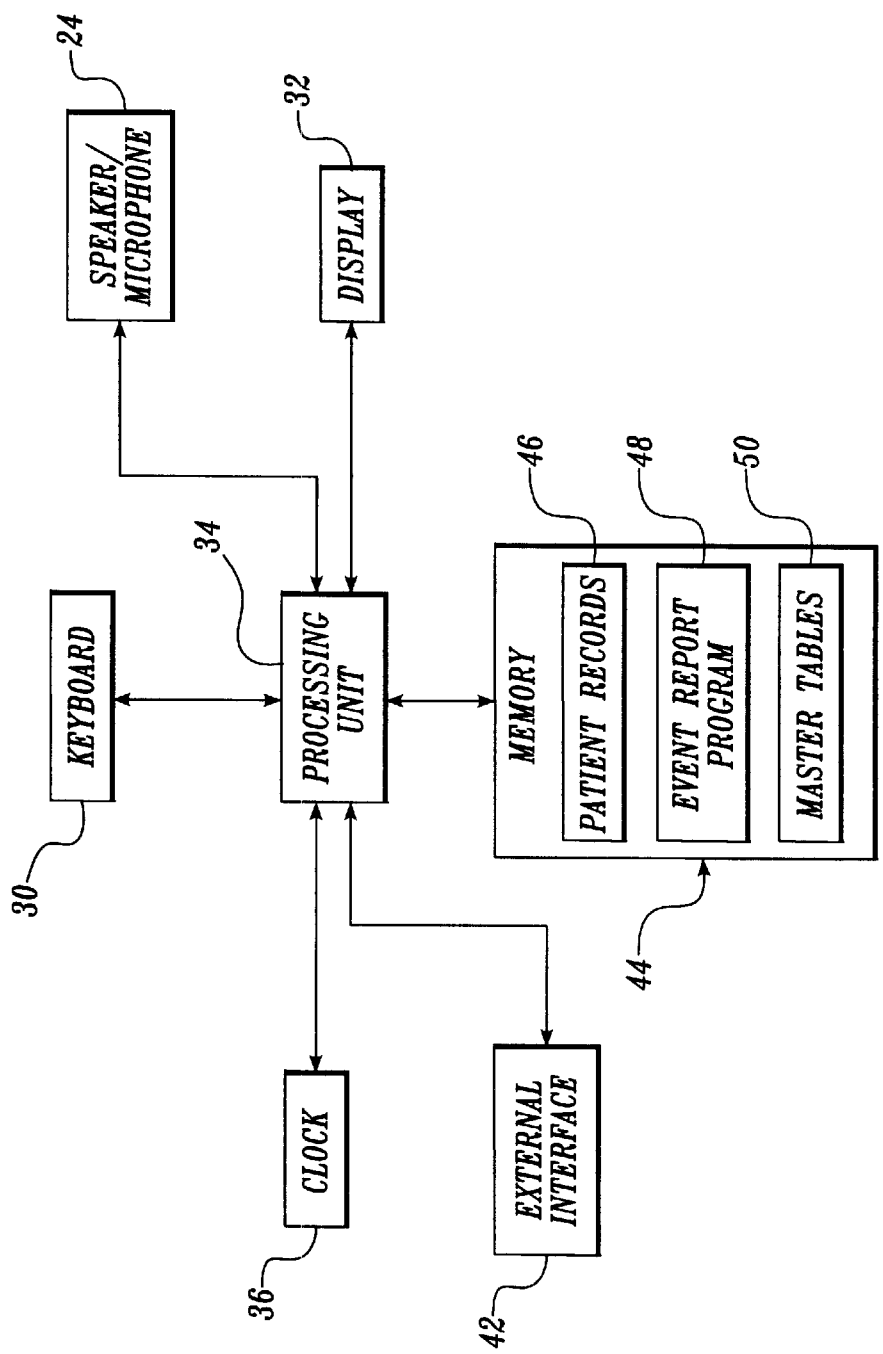
FIG. 2 is a schematic block diagram of the several components of the hand-held computer shown in FIG. 1, that are used to implement the event reporting program and record and report emergency incidents in accordance with the present invention.

FIG. 2 depicts several of the key components of the hand-held computer 20. It will be appreciated by those of ordinary skill in the art that the hand-held computer 20 includes many more components than those shown in FIG. 2. However, a disclosure of an actual embodiment for practicing the present invention does not require that all of these generally conventional components be shown. The hand-held computer 20 includes a processing unit 34 coupled to the touch screen display 32 and a memory 44. The memory 44 comprises a conventional disc, read-only memory, and a random access memory for storing the event report program 48 of the present invention, as well as a set of patient records 46 and a set of master tables 50. The set of patient records 46 consist of a record 46 for each patient treated during an emergency incident. Each patient record 46 includes all of the events and related information recorded by the emergency service provider, including but not limited to personal and background information for the patient, a clinical narrative of the incident, and each event recorded during the incident. The master tables 50, on the other hand, store patient independent information, such as address books, drug guidelines and other reference materials commonly used by emergency service providers in treatment of patients and made available by the event reporting program 48 as described in more detail below. In addition, the master tables 50 store various menus from which the emergency service provider may select predefined events and other information for recordation during the incident. Consequently, the emergency service provider need not manually input each event as it occurs.

Those of ordinary skill in the art will appreciate that due to the limited memory space in hand-held computer 20, the patient records 46 containing the patient and incident information input by the emergency service provider, and the master tables 50 containing patient independent information are stored in simple tables in memory 44 of the hand-held computer 20. If the event reporting program 48 were installed in a more sophisticated device, such as a personal computer or laptop computer, with greater memory capabilities, the patient records 46 and master tables 50 would be stored in a database capable of being accessed and manipulated by a wider variety of database tools. In some embodiments of the present invention, the database in which the patient records are stored comprises a relational database which can be more flexibly accessed and manipulated.

As also shown in FIG. 2, the processing unit 34 is coupled to a keyboard 30 and a microphone/speaker 40 which may be used in addition to or instead of the touch screen 32 and pen 22 to input events and related incident information and control the event reporting program 48. As will be described in more detail below, each event input by an emergency service provider via the touch screen pen 22 and display 32, the microphone/speaker 40, and/or the keyboard 30 is stored in a patient record 46 in memory 44 with the time the event is input as provided by a clock 36 coupled to the processing unit 34.

Finally, the hand-held computer 20 includes an external interface 42 through which the hand-held computer 20 may transfer recorded events and related information to and from the hand-held computer 20 and an external device. For example, in some embodiments of the present invention, the hand-held computer 20 may import events and related information through the external interface 42 from a remote Computer-Aided Dispatch (CAD) system or from another medical device such as a defibrillator. Conversely, the hand-held computer 20 may export events and related information stored in the patient records 46 and master tables 50 of the memory 44 through the external interface 42 to a remote device, such as a computer located at the hospital to which the patient will be admitted. In one actual embodiment of the present invention, the external interface 42 comprises a modem which will establish a communications link with the external device with which the hand-held computer is communicating. In yet other embodiments of the present invention, the external interface 42 comprises serial input and output ports directly connected to the external device with which the hand-held computer is communicating.

Figure 3:
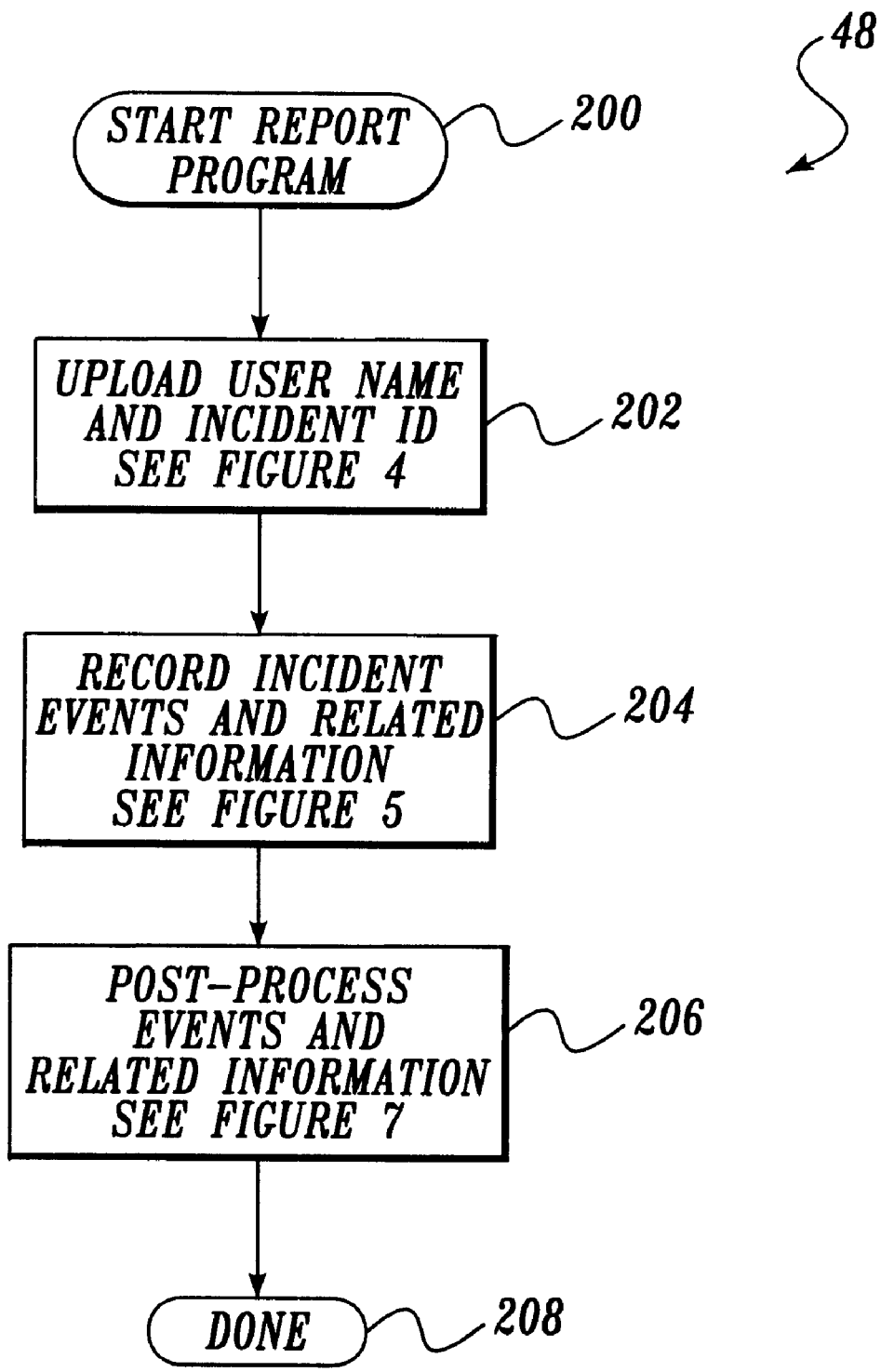
FIG. 3 is a flow chart illustrating the logic used by the event reporting program to record and report emergency incidents.
Figure 4:
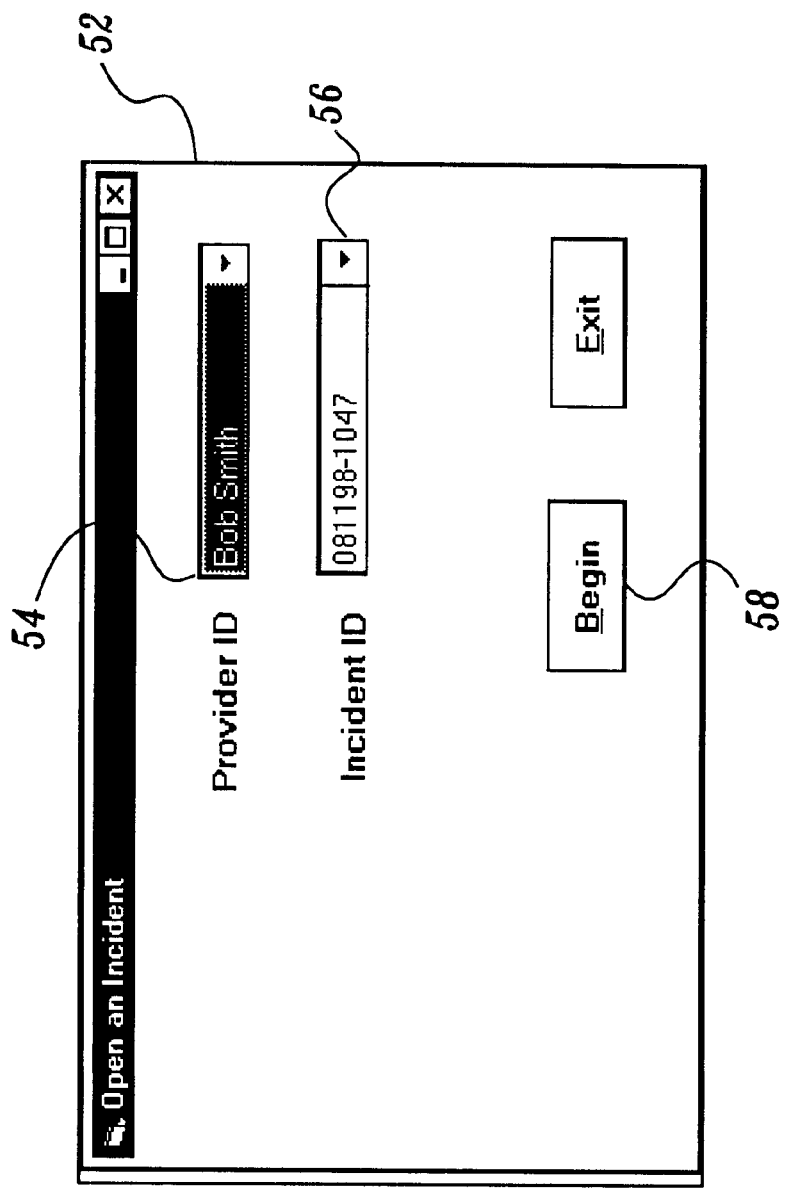
FIG. 4 depicts an initial incident reporting window produced by the event reporting program recording incident identification information.

Now that the components of the hand-held computer 20 which are necessary for implementing the event reporting program 48 of the present invention have been described, the event report program 48 itself will be described in further detail. FIG. 3 illustrates the logic used by the event reporting program 48 to record and report an emergency incident. It will be appreciated that the event reporting program 48 will typically be started up by the emergency service provider on route to the emergency incident or soon after arriving. Accordingly, the event reporting program 48 begins in a block 200 and proceeds to a block 202 in which the emergency service provider uploads a user identification, e.g., the name of the emergency service provider, and an identification number for the incident. More specifically, the event reporting program 48 produces an open incident window 52 on the display 32 of the hand-held computer 20 as shown in FIG. 4 through which the emergency service provider enters his or her name in a user identification field 54, as well as the incident identification number in an incident identification field 56. It will be appreciated that the user's identification and the incident's identification number may be entered by the emergency service provider using the keyboard 30 of the hand-held computer 20 or voice prompting via the speaker/microphone 24, or by selecting the provider identification and the incident identification from predefined menus. Once the necessary information has been input, the emergency service provider may continue with the event reporting program 48 by selecting a begin button 58.

Returning to FIG. 3, the event reporting program 48 proceeds to a block 20 in which the emergency service provider begins recording events that occur during the emergency incident. As will be described in more detail below, the emergency service provider may record events which occur during the emergency incident using a series of windows produced by the event reporting program 48. The emergency service provider may also input additional information regarding the incident and the patient being treated. Following the incident, the emergency service provider may further process the events and related information that were recorded during the incident in order to produce a more accurate run report regarding the entire incident. In this regard, the event reporting program 48 post-processes the events and related information in a block 206. Once post-processing is complete, the event reporting program 48 ends in a block 208.

Returning to block 204, once the name of the service provider and the identification number for the incident have been uploaded via the open incident window 52, the event recording component of the event reporting program 48 is instigated. The logic implemented by the event recording component of the program is shown in more detail in FIG. 5. The logic begins in a block 210 and proceeds to a block 212 where the "arrive patient" data for the incident is automatically stored in the patient's record 46. In this regard, the event reporting program 48 generates an event recorder window 60 as shown in FIG. 6A. The event recorder window 60 includes an event summary 62 which displays an event record 68 for each event recorded by the emergency service provider during an incident. Each event record 68 essentially comprises an event/time pair, i.e., a description of the event itself and a time at which the event occurred. The description of the event itself can be broken down into a common descriptor for the event, e.g., "arrive patient" or "shock," and additional detail for the event, e.g., "200J" for a shock event. Similarly, the time at which the event occurred may be broken down into a time as read by the clock 36 at which the event was input by the emergency service provider (which should approximate the time the actual event occurred within one minute if promptly input by the emergency service provider), and an expected time for the event to occur (which can be determined based on the time registered by the clock 36 and a time interval during which the event is expected to occur according to EMS and other accepted guidelines). As will be described in more detail below, the emergency service provider can input a treatment protocol comprising a collection of predefined events (wherein each predefined event is associated with an expected time of occurrence), rather than input events individually, one-by-one as they occur. It will be appreciated that each event record 68 and thus, each event/time pair, may include either an actual time, an expected time, or both. Each event/time pair must also include an event description, although additional detail is not always required. Each event record 68 comprising an event/time pair is represented in the event summary 62 with a time field 68a containing the time as registered by the clock 36 at which the emergency service provider input the event; an expected time field 68b containing an automatically logged time at which the event is expected to occur during the incident; an event field 68c containing a common descriptor for the event input by the emergency service provider; and a detail field 68d containing additional detail and information regarding the event. As will be described in more detail below, an event record 68 will be added to the event summary 62 contained in the event recorder window 60 as each event occurs and is input by the emergency service provider during the incident.

As mentioned above, there are a number of ways in which the emergency service provider may record events and related information via the event recorder window 60. For example, the emergency service provider may add individual events and related detail by inputting an event descriptor in an event selection field 64 and inputting related information in a detail field 66 in the event recorder window 60. In addition, the emergency service provider may select a treatment protocol, i.e., a predefined set of events, to the event summary window 62 from the protocol selection field 70. Finally, the emergency service provider can initiate a variety of tools from the event recorder window 60 to aid in treatment of the patient during the incident. For example, the emergency service provider may initiate an address book tool by selecting an address book button 72a; a drug guide tool by selecting a drug guide tool button 72b; a medication tool by selecting a medication tool button 72c; a narrative tool by selecting a narrative tool button 72d; a stopwatch tool by selecting a stopwatch tool button 72e; and a dosage calculating tool by selecting dosage tool button 72f.

Figure 5:
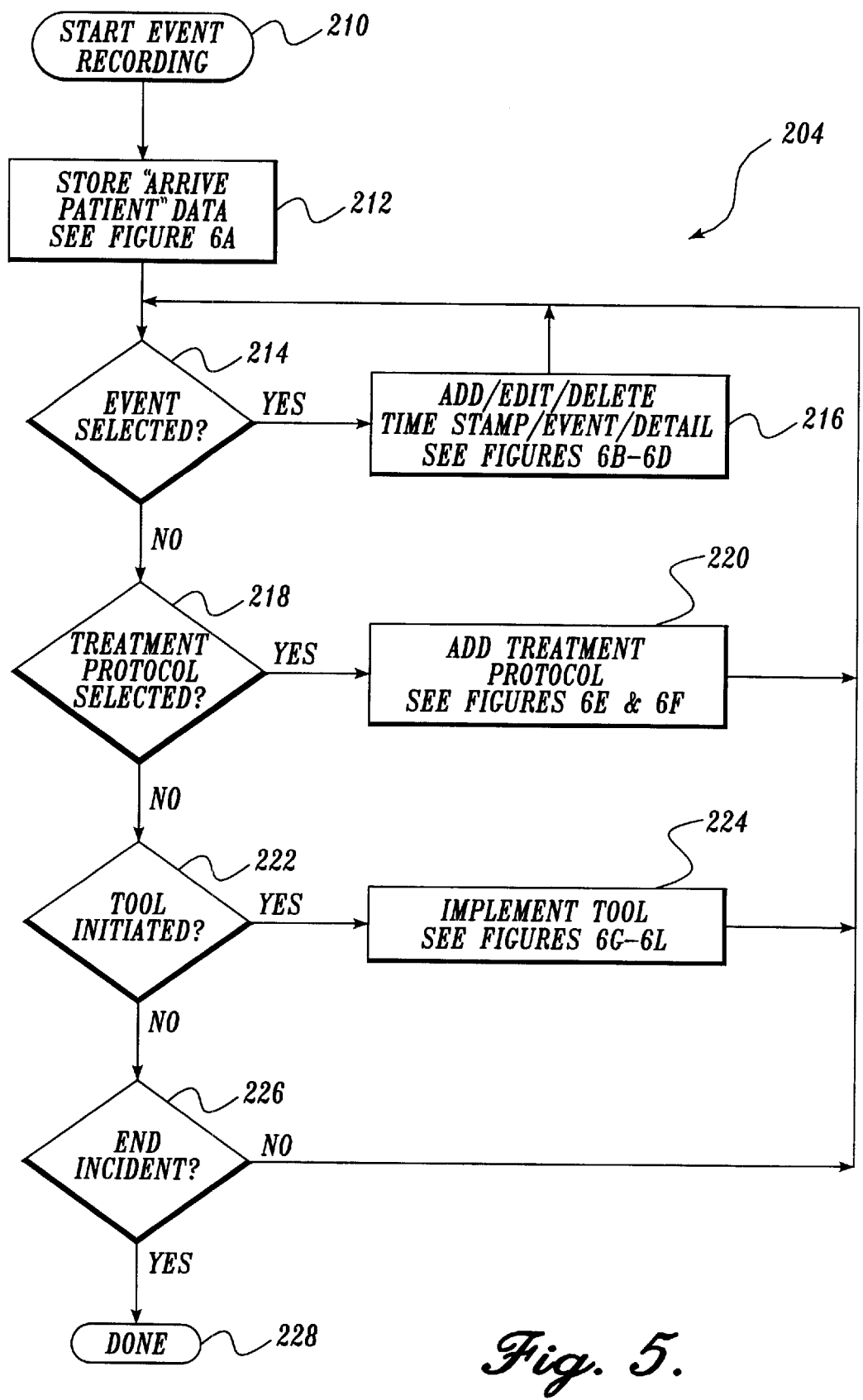
FIG. 5 is a flowchart illustrating the logic used by the event reporting program to record events and related information during the emergency incident.
Figure 6A:
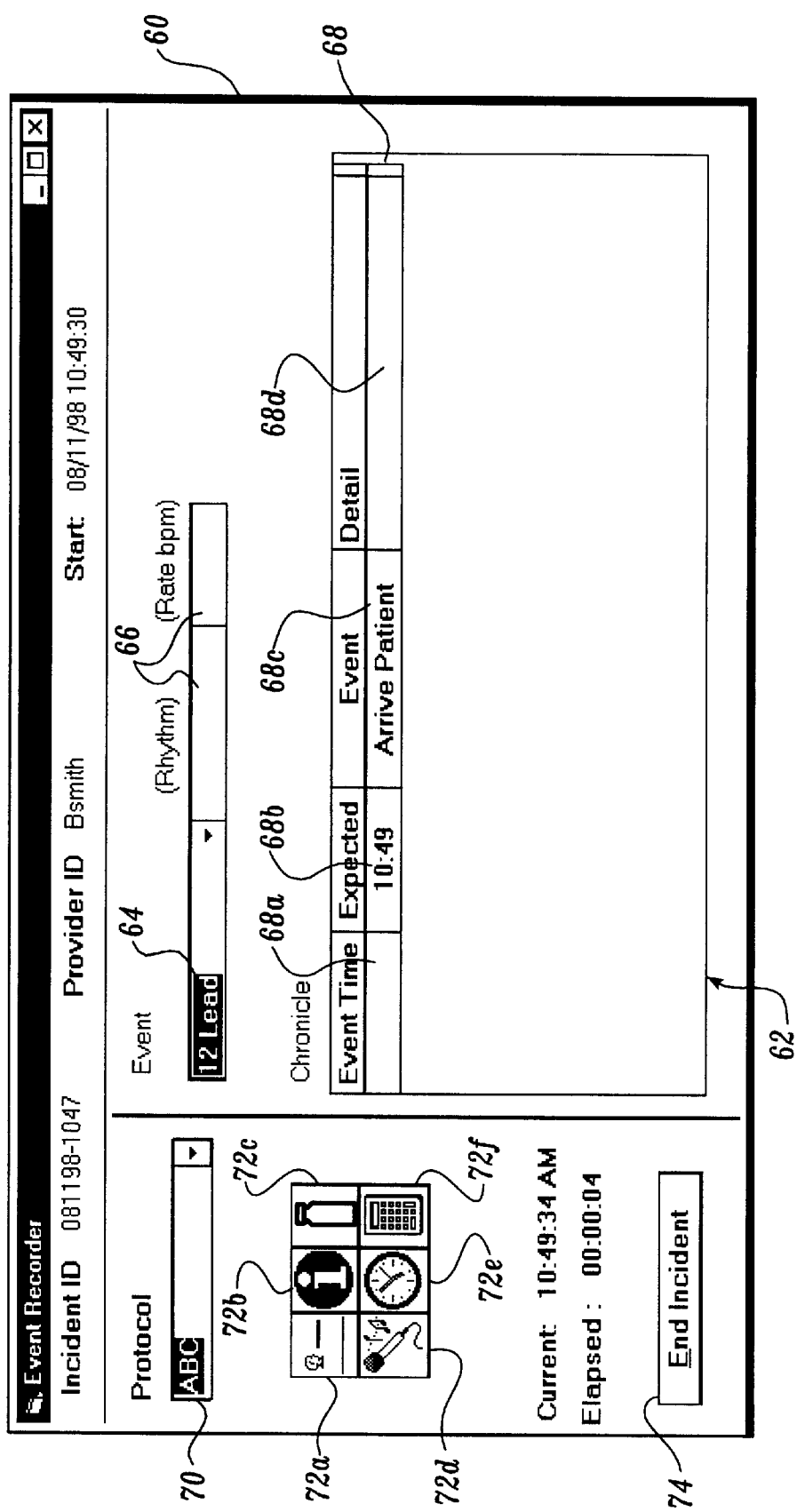

Returning to block 212 of FIG. 5 and the arrival of the emergency service provider to the emergency incident, it will be appreciated that the event reporting program 48 automatically adds an event record 68 to the event summary 62 to record the arrival of the emergency service provider to the patient. More specifically, an event record 68 is added to the event summary 62 as soon as the emergency service provider begins the event recordation component of the program from the open incident window 52. The expected time for the arrive patient event is stored in the expected time field 68b of the event record 68. It will be appreciated that the expected time entered in this field is the time calculated by the event reporting program 48 based on the actual time provided by the clock 36 and a time interval during which the emergency service provider is reasonably expected to arrive at the patient. It will be appreciated that the calculation of this time interval will depend on the acceptable emergency response intervals promulgated by the provider's supervisory EMS. The event descriptor, i.e., "arrive patient" is also automatically entered in the event field 68c of the event record 68. The event record is correspondingly stored in the patient record 46 for the patient in memory 44. As will be described in more detail below, event records 68 can be further modified, added or deleted by the emergency service provider as necessary to provide a more accurate run report for the emergency incident. In addition, event records 68 may be exported to other devices for further processing and record keeping.

Returning to FIG. 5, once the arrive patient event record has been stored and displayed as part of the event summary 62, the emergency service provider is free to add additional events as they occur during the incident, add treatment protocols as the emergency service provider deems necessary, and initiate the various tools described above as appropriate. In this regard, the event recording program 48 proceeds to a decision block 214 where it determines if the emergency service provider has selected to add, modify or delete an event record 68 from the event recorder window 60. If so, the emergency service provider may add, edit, or delete an entire event, the actual time associated with an event, or the detail associated with an event in a block 216. The event recorder windows 60 associated with such actions are shown in more detail in FIGS. 6B–6D.

Figure 6B:
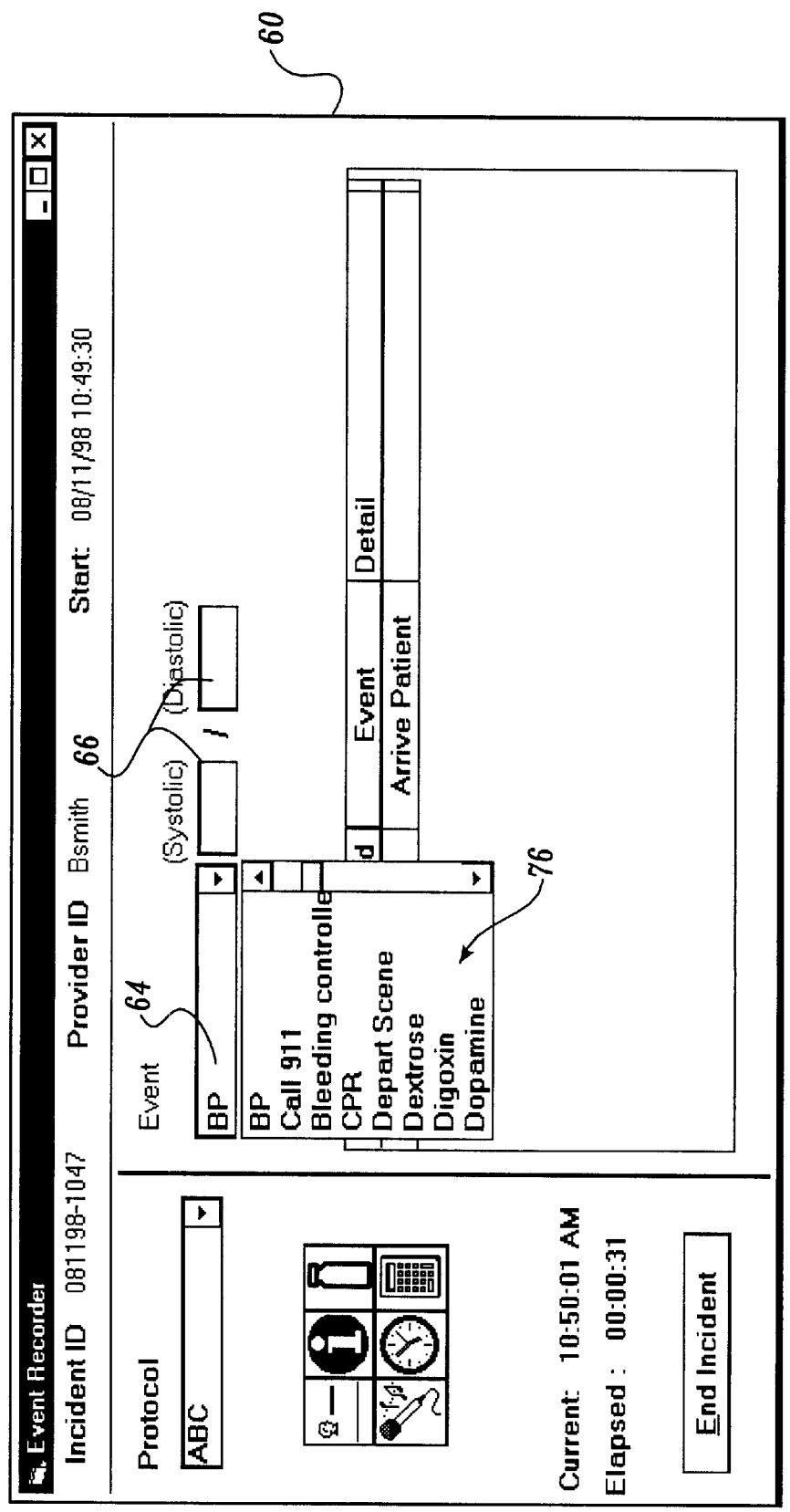

Referring to FIG. 6B, the emergency service provider may open an event menu 76 by tapping the touch screen pen 22 on the arrow of the event selection field 64. The emergency service provider may then highlight the desired event descriptor from the menu of events displayed in the event menu window 76 using the touch screen pen 22. For example, if the next event in the incident that occurs is the measurement of the patient's blood pressure, the emergency service provider may select the blood pressure event descriptor, i.e., "BP," from the event menu 76 by either manually using the touch screen pen 22 or via voice prompt using the speaker/microphone 24. The blood pressure event descriptor, "BP", will then appear in the event selection field 64 as shown in FIG. 6B. The emergency service provider then may input additional detail regarding the blood pressure event either via the keyboard 30 or the speaker/microphone 24. More specifically, the emergency service provider may input the systolic and diastolic pressures measured from the patient in a detail entry field 66. As noted above, the menu of events displayed in the event menu window 26 is stored in memory 44 in the master tables 50. If the displayed menu of events does not include the event desired by the emergency service provider, it will be appreciated that the provider may simply input the desired event descriptor using the keyboard 30 or via voice prompt using the speaker/microphone 24. If voice prompting is used, the actual voice recording may be stored in memory 44 for later retrieval, reference, and/or transcription.

Figure 6C:
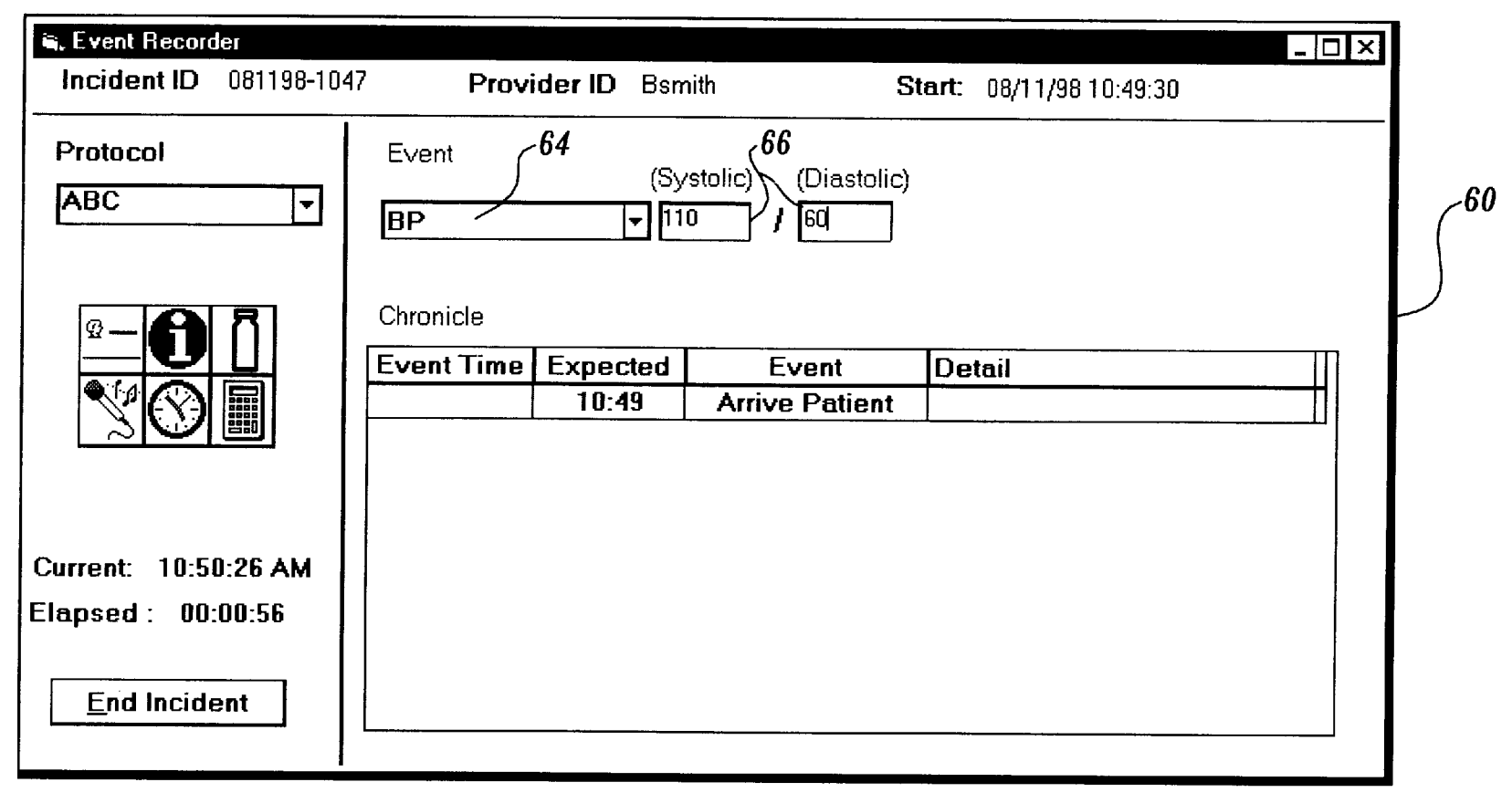
Figure 6D:
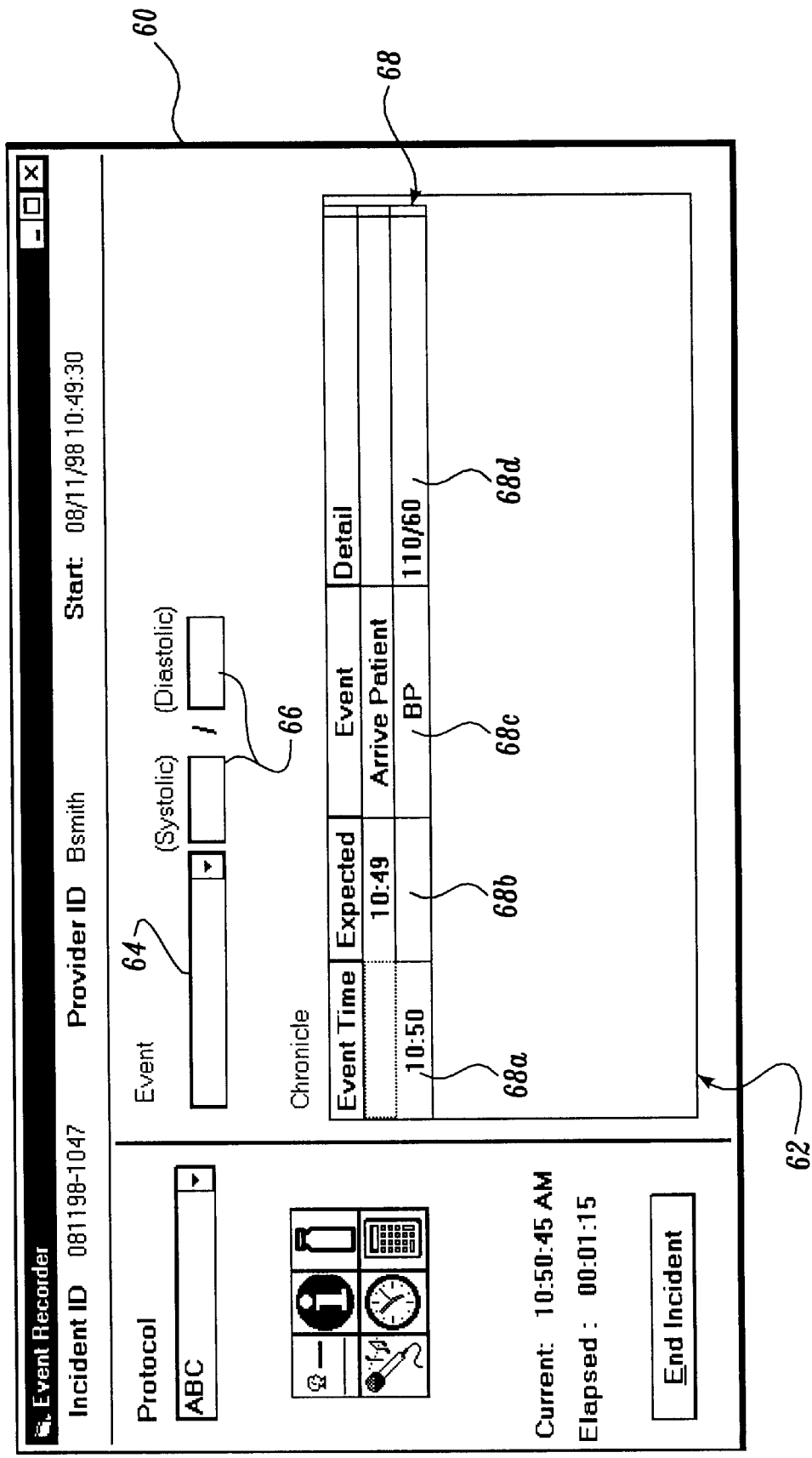

As shown in FIG. 6C, once the event selection field 64 and perhaps also, the detail entry fields 66 have been completed by the emergency service provider, the event reporting program 48 automatically adds an event record 68 containing the corresponding event/time pair to the event summary 62 as shown in FIG. 6D. The event record 68 includes the time at which the blood pressure was measured, i.e., the time registered on the hand-held computer's clock 36 when the blood pressure event was selected, in the event time field 68a of the event record 68. The event descriptor, "BP," is inserted in the event field 68c of the event record 68; and the event detail, i.e., the measured systolic and diastolic pressures, are inserted in the detail field 68d of the event record 68. Those of ordinary skill in the art will appreciate that for every event descriptor selected by the emergency service provider from the event menu 76 or input manually by the provider, a similar event record 68 will be added to the event summary 62. Further, it will be appreciated that the event record 68 is stored in the patient's record 46 in memory 44 of the hand-held computer 20 for post-processing or for export to another device.

Returning to block 216 of FIG. 5, in addition to adding an event record 68 to the event summary 62, the emergency service provider can also edit or delete an event record 68. More specifically, if the emergency service provider wishes to modify an already added event record 68, the emergency service provider need merely highlight the appropriate field 68a–68d of the event record using the touch screen pen 22 or using voice input via the speaker/microphone 24 in order to modify the data contained in that field. For example, if the emergency service provider wishes to add additional detail in the detail field 68, the emergency service provider can merely tap the data entry field 68d with the touch screen pen 22 and then add, modify or delete the information contained therein using the keyboard 30 of the hand-held computer 20 or voice prompting via the speaker/microphone 24. The same procedure can be followed to modify, add or delete any of the data stored in any of the other fields 68a, 68b, and 68c. Further, if the emergency service provider wishes to delete an event record in its entirety, the emergency service provider must merely highlight the entire record and enter the delete key (not specifically shown) contained on the keyboard 30 of the hand-held computer. As will be described in more detail below, the emergency service provider also has the option of editing, modifying, or deleting event records after the incident during post-processing.

Referring once again to FIG. 5, once the emergency service provider has added, edited or deleted an event record 68, the logic returns to decision block 214 where the emergency service provider is again given the opportunity to add, modify or delete an event and/or its associated time stamp and detail. Accordingly, as treatment of the patient progresses during an emergency incident, the emergency service provider can record each event which occurs during treatment using the event reporting program 48. However, returning to decision block 214, the emergency service provider may, in fact, choose not to add an individual event. Rather, the provider may choose to record an entire treatment protocol as previously mentioned. In this regard, the event reporting program 48 determines in a decision block 218 if the emergency service provider has selected a treatment protocol from the treatment protocol field 70 of the event recorder window 60. If so, the event reporting program 48 automatically adds the treatment protocol to the event summary 62 in a block 220.

Figure 6E:
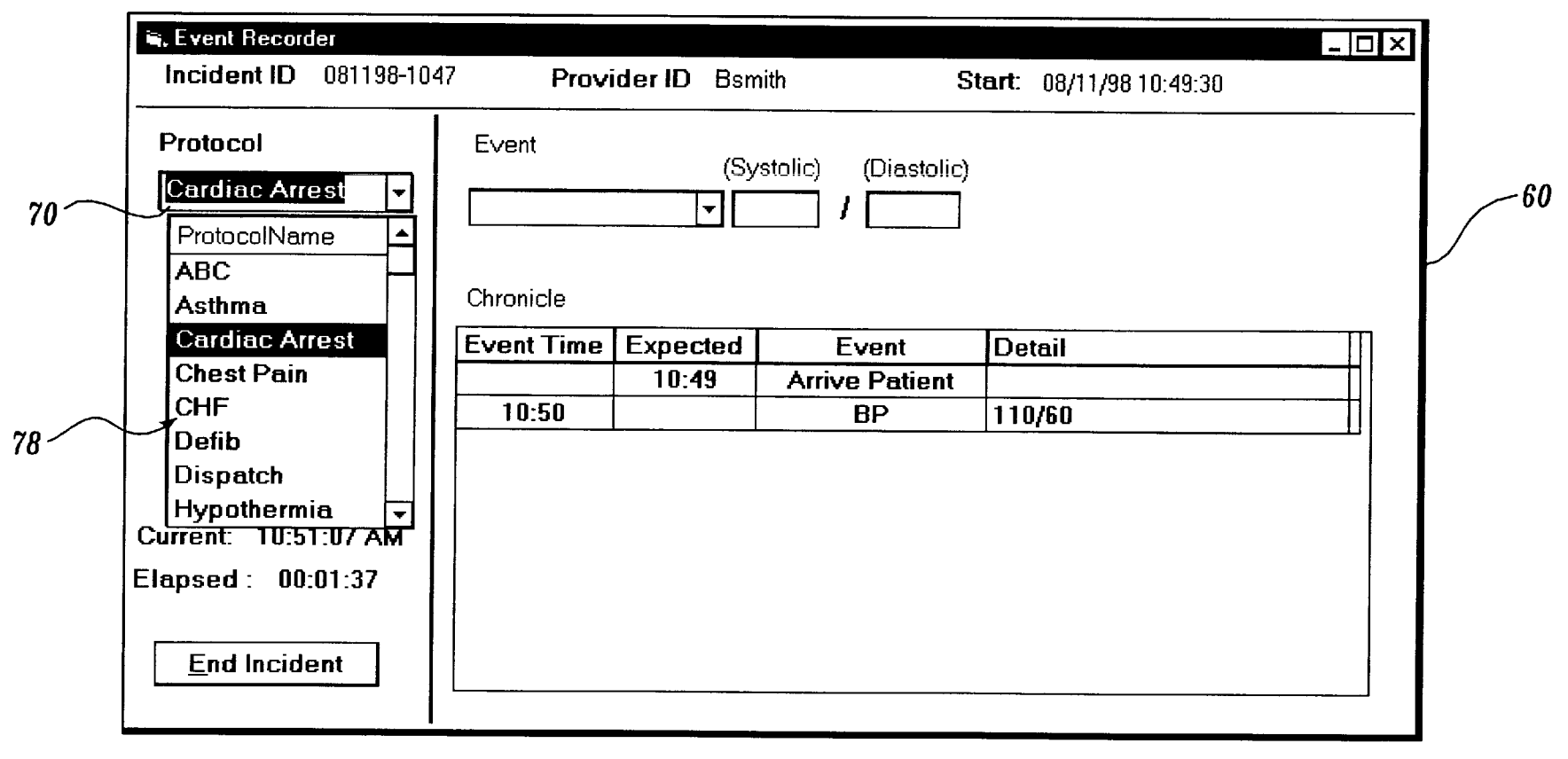
Figure 6G:
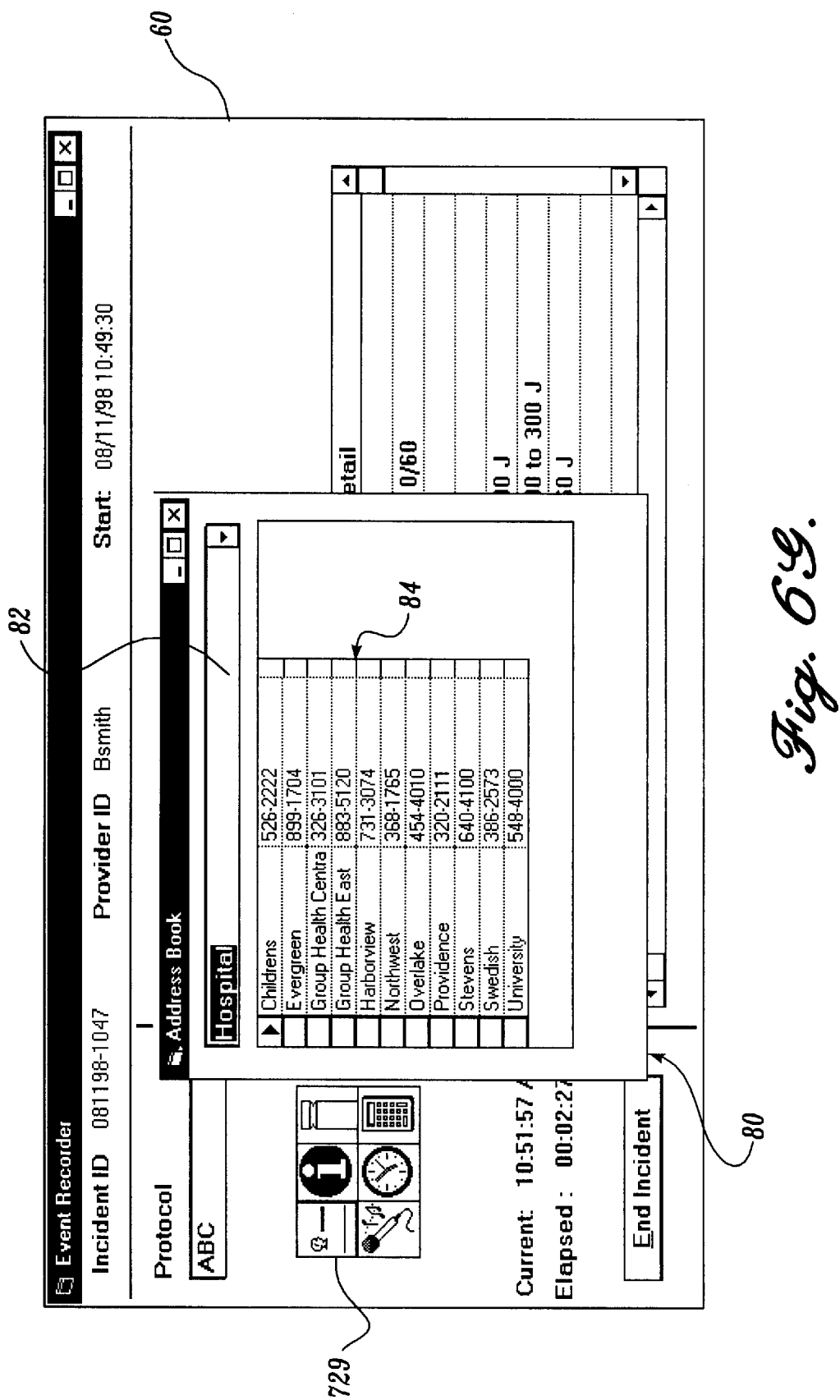
Figure 6I:
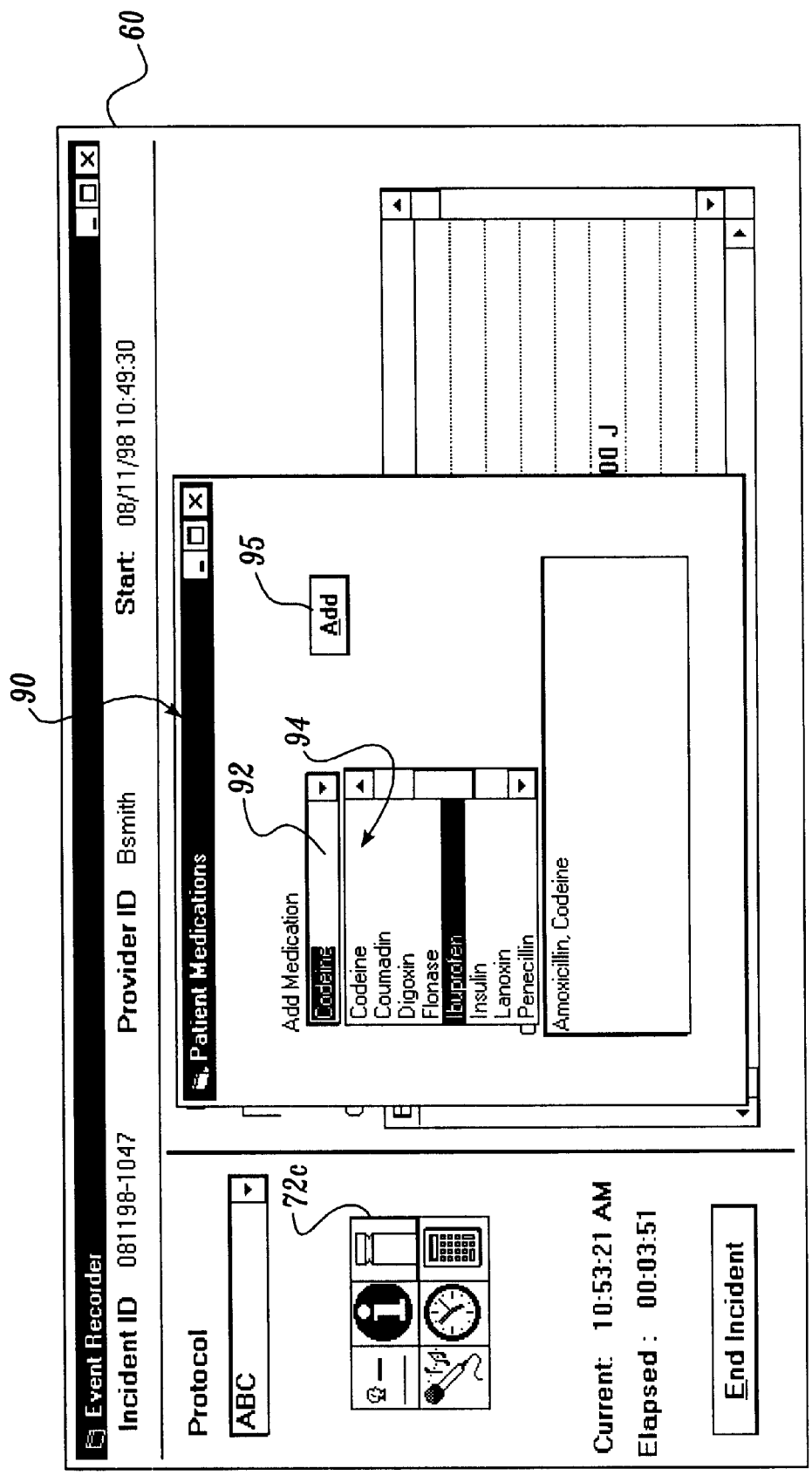
Figure 6F:
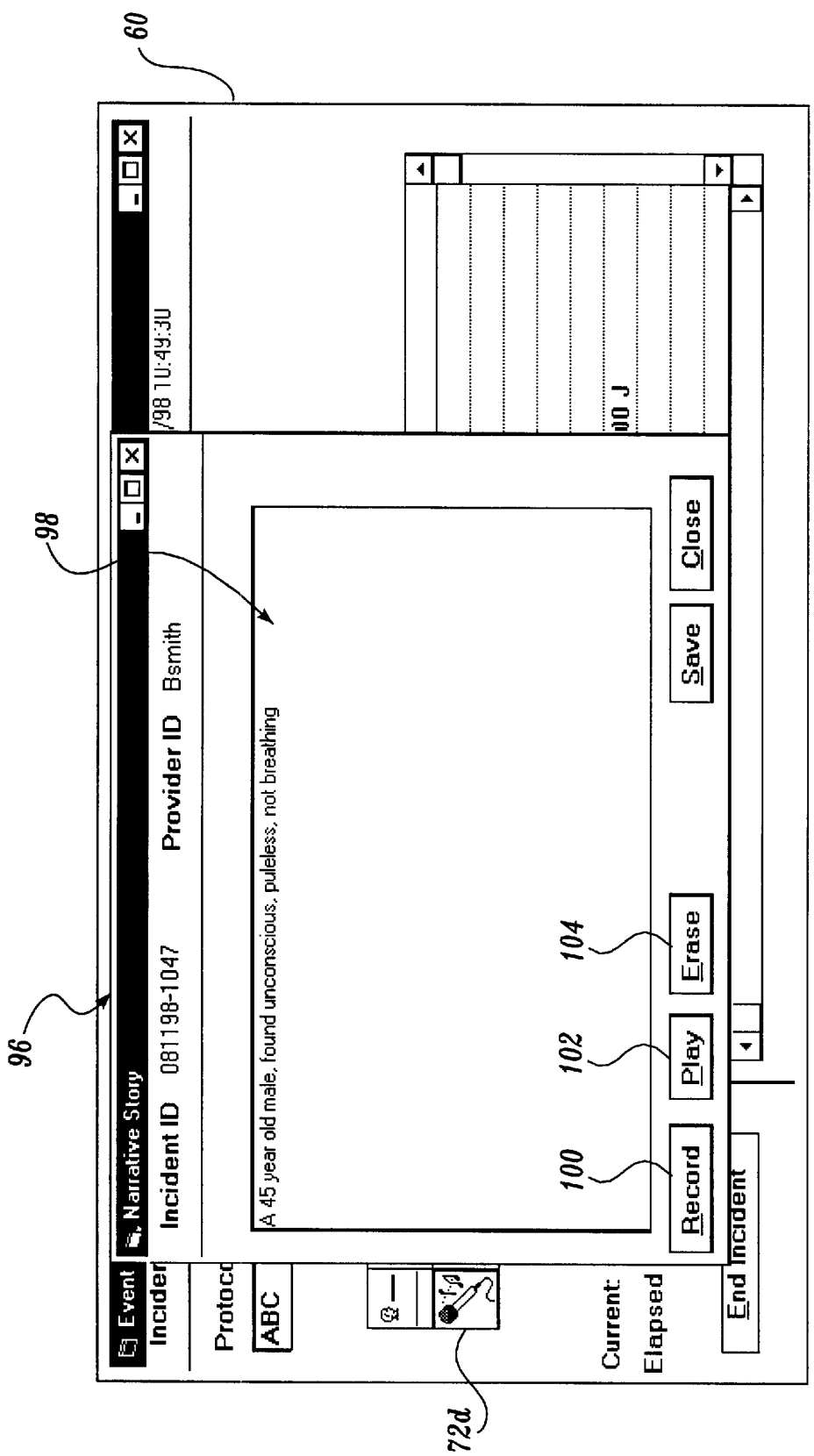

The event recorder window 60 produced by the event recording program 48 when a treatment protocol is added is shown in more detail in FIGS. 6E and 6F. Referring to FIG. 6E, the emergency service provider may select a treatment protocol by opening a protocol menu 78 and highlighting the desired protocol. For example, if the patient is experiencing cardiac arrest, the provider may wish to record a treatment protocol for cardiac arrest which includes all of the events one would most likely expect to occur during treatment of such a condition, e.g., CPR, delivery of a therapeutic shock, etc., and the time at which each of these events are expected to occur. Consequently, the emergency service provider need not record each event associated with treatment of the cardiac arrest one-by-one, and is free to give his or her full attention to the patient. However, as will be described in more detail below, the provider does have the ability to modify and delete any of the events added by selecting a protocol as necessary to create a more accurate run report. In addition, it will be appreciated from the description above that the provider can also record additional events that may have occurred during treatment but were not included in the selected protocol.

As shown in more detail in FIG. 6F, once the desired protocol has been selected (e.g., "Cardiac Arrest") a predefined collection of event records 68 associated with treatment in accordance with the selected protocol is entered in the event summary 62. Again, using the cardiac arrest example, the first event that typically occurs in the treatment of cardiac arrest is the performance of CPR. Accordingly, the event reporting program 48 enters an event record 68' for CPR, wherein the event record includes the time at which the emergency service provider is expected to perform CPR in the expected time field 68b. In addition, the event reporting program will insert a descriptor for the event, i.e., "CPR", in the event field 68c. As yet another example, subsequent to performing CPR and monitoring the patient, the provider is expected to deliver a therapeutic shock to the patient. Accordingly, the treatment protocol includes an event record 68" containing the expected time of the shock in expected time field 68b, an event descriptor for the shock in event field 68c, and additional detail regarding the shock, e.g., 200J, in detail entry field 68d. In accordance with yet other aspects of the present invention, once the expected time stored in the expected time field 68b for each protocol related event record expires, the event reporting program issues an audible alarm via the speaker/microphone 24 and/or a visual alarm via the display 32 to notify the emergency service provider that the expected treatment event must be administered.

As is apparent from the logic illustrated in FIG. 5, once the treatment protocol has been added in a block 220, the logic returns to decision block 214 where it determines if the emergency service provider has elected to add, edit or delete an event record 68. It follows that once a treatment protocol has been added to the event summary 62, the emergency service provider can continue to add additional event records 58 to the event summary 62, or can modify or previously recorded event records, including those added in association with a treatment protocol. Thus, if the emergency service provider modifies the treatment of the patient in any way from that automatically defined by the protocol, the emergency service provider is capable of modifying or deleting the appropriate event records, thus making for a more accurate incident run report.

Returning to FIG. 5, in addition to adding, editing or deleting event records 68 individually and in groups by selection of a treatment protocol, the emergency service provider may also initiate tools from the event recorder window 60 to assist him or her in treatment of the patient. In this regard, the logic proceeds to a decision block 222 where it determines if the emergency service provider has initiated a tool by selecting one of the tool buttons 72a–72f from the event recorder window 60. If so, the selected tool is implemented by the event reporting program 48 in block 224. The event recorder windows 60 associated with each tool are shown in more detail in FIGS. 6G–6L.

As shown in FIG. 6G, if the emergency service provider selects the address book button 72a, an address book window 80 is generated by the event reporting program 48. From the address book window 80, the emergency service provider may open an address menu 84 and select a desired address or telephone number using the touch screen pen 22. For example, if the emergency service provider needs the telephone number for a particular hospital, the emergency service provider may select the phone number for the desired hospital from the address menu 84.

If the emergency service record 68 provider selects the drug tool button 72b, a drug guideline window 86 is generated by the event reporting program 48 as shown in FIG. 6H. The emergency service provider may then retrieve from the master tables 50 stored in memory 44 of the hand-held computer, the guidelines for any drug with which the emergency service provider desires to treat the patient. The emergency service provider merely selects the desired drug from a drug menu (not shown) opened by tapping an arrow in a drug identification field 88 of the drug guideline window 86 with the touch screen pen 22 or by voice command. The associated information is retrieved from the master tables 50 stored in memory 44 and displayed in the drug guideline window 88. Once information regarding the desired drug has been retrieved and displayed, the emergency service provider may opt to calculate an appropriate dosage for the drug by selecting a dose button 89. The dosage calculation tool and the dosage calculation window 118 generated by the event reporting program 48 will be described in more detail below.

If the emergency service provider selects the patient medications button 72c in the event recorder window 60, a patient medications window 90 is generated by the event reporting program 48 as shown in FIG. 6I. The emergency service provider may then select any medication the patient is currently taking from a medication menu 94 (supplied by the master table 50). This medication information is then stored in memory 44 in the patient's record 46.

If the emergency server provider selects the narrative button 72d, the event reporting program 48 generates a narrative story window 96 on the display 32 of the hand-held computer 20 as shown in FIG. 6J. The narrative story window 96 includes a narrative field 98 into which the emergency service provider may directly input information in a narrative format. It will be appreciated that the emergency service provider may input the narrative using the keyboard 30 of the hand-held computer 20. However, in other embodiments of the present invention, in which the hand-held computer is equipped with a speaker/microphone 24 and voice recognition software, the emergency service provider may simply speak into the microphone 24 in order to input the narrative. If voice prompting is used, the emergency service provider may simply select a record button 100 using the touch screen pen 22 to initiate recording of his voice via the speaker/microphone 24. If the emergency service provider wishes to play back the recorded narrative, the emergency service provider may select the play button 102 and if the, emergency service provider wishes to erase any of the narrative, the emergency service provider may select the erase button 104. Once the narrative has been recorded, the emergency service provider may exit the narrative story window 96 by selecting the close button 103. Once completed, the text of the narrative is stored in the patient's record 46 in memory 44 of the hand-held computer 20.

Figure 6K:
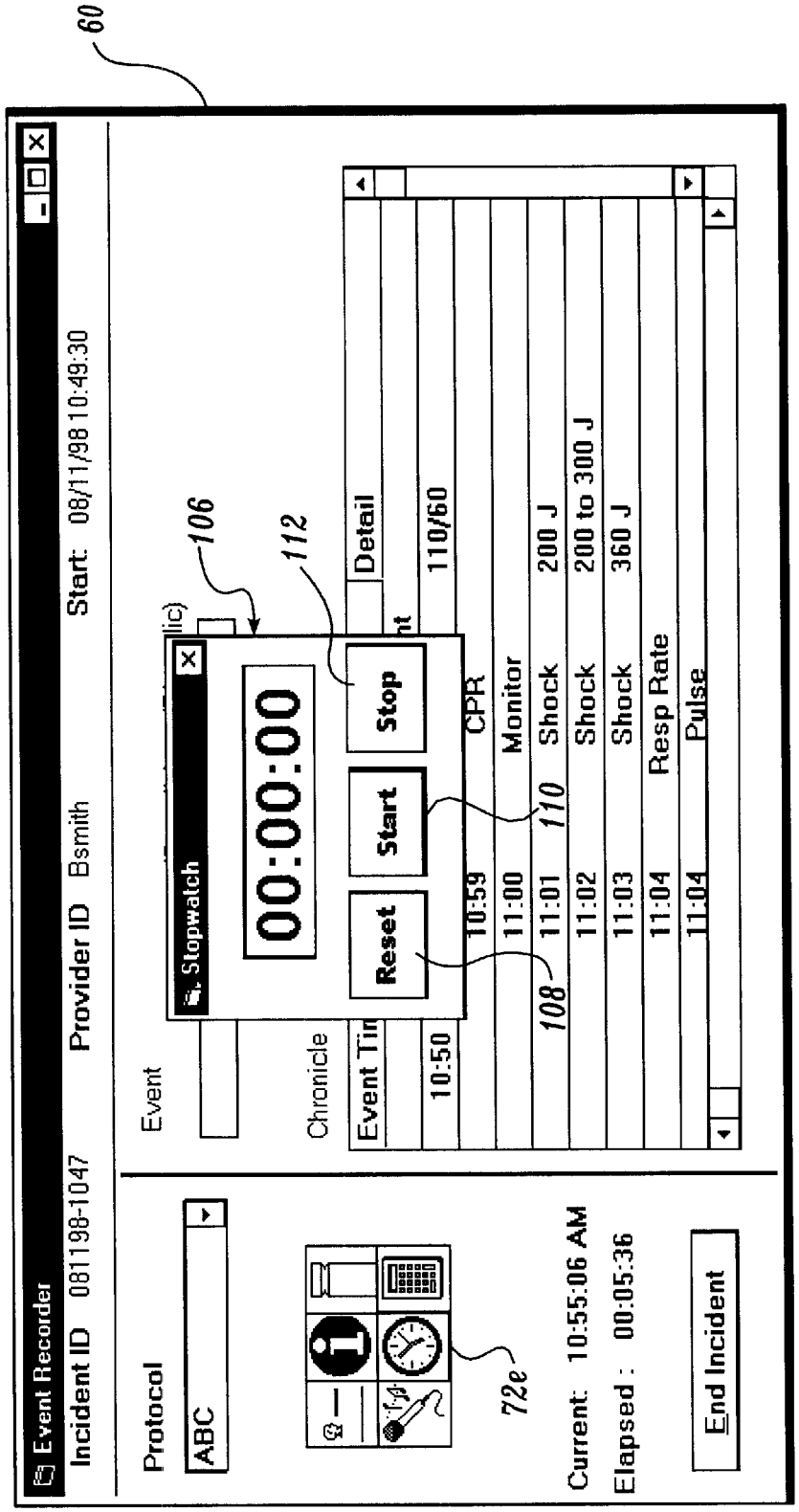

If the emergency service provider selects the stop watch tool button 72e, a stop watch window 106 is generated by the event reporting program 48 as shown in FIG. 6K. The stop watch tool allows the emergency service provider to time events, e.g., to time a particular treatment measure. For example, if the patient's pulse must be taken for sixty seconds, the emergency service provider may reset the stop watch to sixty seconds using the reset button 108 and start the countdown of the stop watch from sixty seconds using the start button 110. When the stop watch expires, the emergency event program generates an audible tone via the speaker/microphone 24 of the hand-held computer 20 and/or via a visible message generated on the display. The emergency service provider can stop the stop watch at any time using the stop button 112.

Figure 6L:
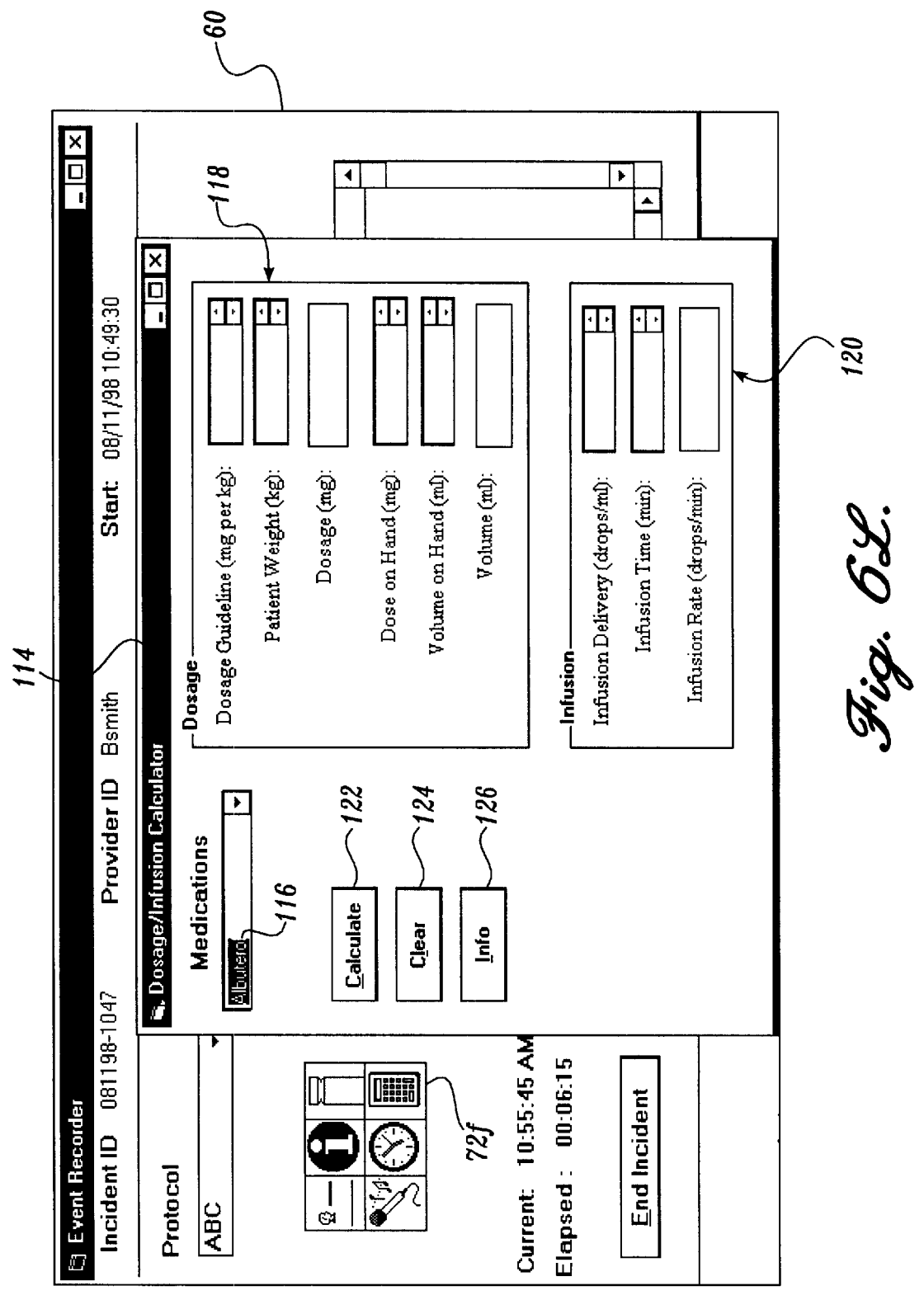

Finally, if the emergency service provider selects the dosage calculation button 72f from the event recorder window 60, the event reporting program 48 generates a dosage/infusion calculator window 114 as shown in FIG. 6L. Accordingly, the emergency service provider may select the desired medication from a medication menu (not shown) opened, for example, by tapping an arrow in a medication field 116 of the dosage/infusion calculator window 114. The emergency service provider may then input the information necessary for calculating the appropriate dosage for the selected medication in a dosage window 118. The provider may also calculate an infusion rate for the selected medication by inputting the necessary information in an infusion window 120. Once the appropriate information for calculating the dosage and/or infusion has been input by the provider, the emergency service provider may select a calculate button 122 to initiate calculation of the appropriate dosage/infusion. Those of ordinary skill in the art will recognize that the appropriate formulas for calculating dosage/infusion are well known in the art and thus, need not be described in more detail herein. If the emergency service provider wishes to calculate the dosage/infusion for another medication, the emergency service provider need only select the clear button 124 in the dosage/infusion calculator window 114. If the emergency service provider desires more information regarding the selected medication, the emergency service provider may select the information button 126 from the dosage/infusion calculator 114. In response, the event reporting program 48 will generate a drug guideline window 86 as shown in FIG. 6H and as associated with the drug guideline button 72b for the selected medication. Finally, as noted above, the emergency service provider may proceed to the dosage/infusion calculator window 118 via the drug guideline window 86 shown in FIG. 6H by selection of the dose button 89 in the drug guideline window 86.

Returning to FIG. 5, once the tool selected by the emergency service provider has been implemented in a block 224, the logic returns to decision blocks 214, 218 and 222 as appropriate depending on the selections made by the emergency service provider. It follows from the above discussion that the emergency service provider may add event records, add treatment protocols and initiate tools in whatever order he or she deems necessary until the incident comes to a conclusion. At that time, the emergency service provider may select an end incident button 74 from the event recorder window 60 and the event recording component of the event reporting program 48 will be terminated. Accordingly, the result of a decision block 226 in FIG. 5 is positive, and the logic ends in a block 228.

Returning to FIG. 3, once the event recording component of the event reporting program 48 has been completed in a block 204, the post-processing component of the event reporting program begins in a block 206. It will be appreciated that the post-processing of the events and related information recorded during the incident may occur at any time. For example, post-processing may occur while the emergency service provider is still at the scene of the incident, or after the provider delivers the patient to an emergency care facility. As will be described in more detail below, regardless of when post-processing occurs, the emergency service provider is allowed by the event reporting program 48 to add, modify and delete previously recorded events; add events recorded by external devices; add, modify and delete information regarding the patient; edit the previously recorded narrative; generate a complete incident run report; and/or export events and related information to external devices.

Figure 7:
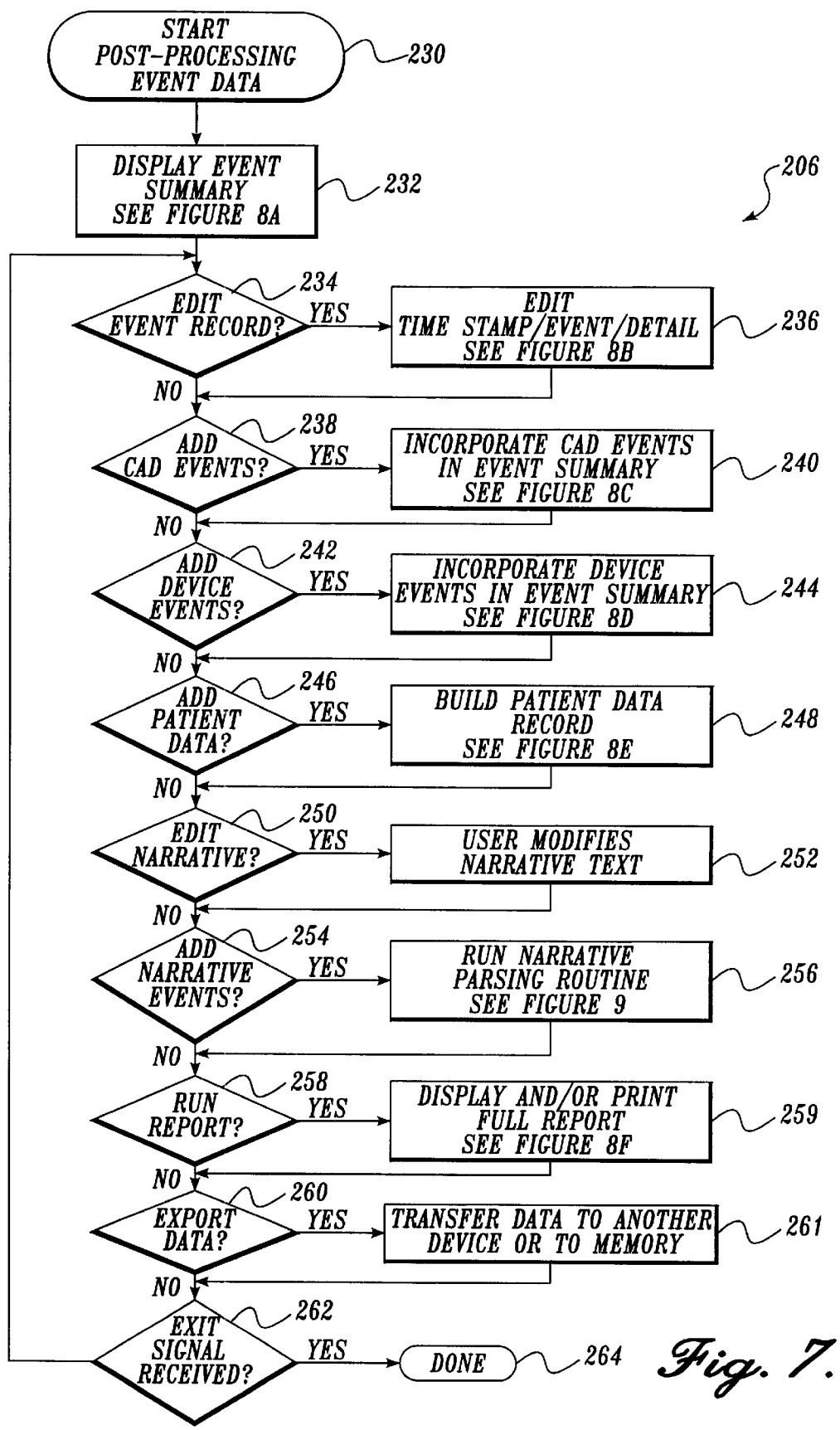
FIG. 7 is a flowchart illustrating the logic used by the event reporting program to further process events and related information after the occurrence of the emergency incident.
Figure 8A:
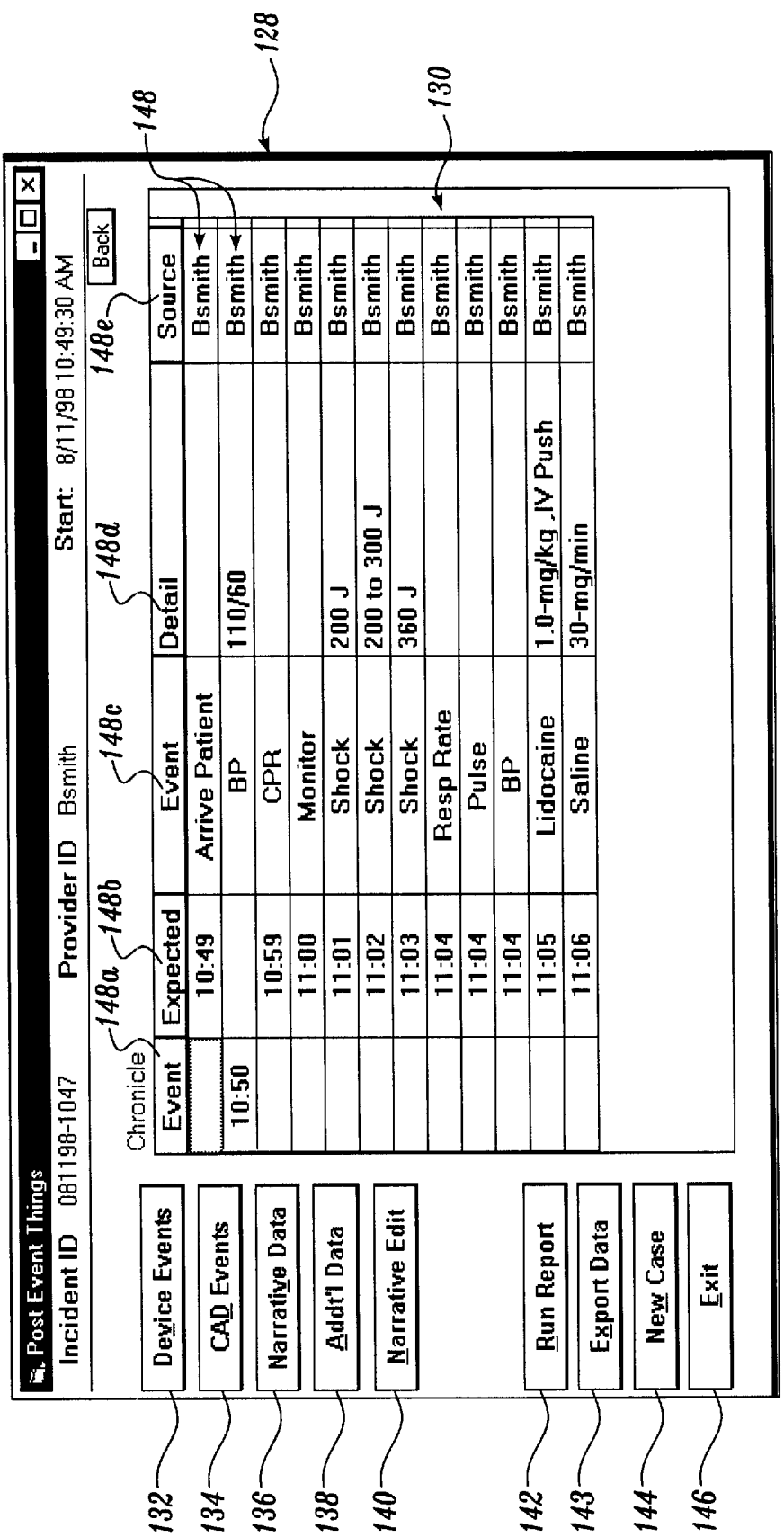

The logic employed by the post-processing component of the event reporting program 48 to post-process events is shown in more detail in FIG. 7. The logic begins in a block 230 and proceeds to a block 232 where the event reporting program 48 generates a post-event window 128 on the display 32 of the hand-held computer 20. The post-event window 128 generated by the event reporting program is shown in more detail in FIG. 8A. Similar to the event recorder window 60, the post-event window 128 includes an event summary 130 which displays a post event record 148 corresponding to each event record 68 that was recorded by the emergency service provider during the incident. Accordingly, each post event record 148 includes a time field 148a, an expected time field 148b, an event field 148c and a detail entry field 148d. However, the post event record 148 also includes a source field 148e which identifies the source of the recorded event. For example, if the event was recorded by the emergency service provider, the event reporting program 48 automatically enters the user identification of the emergency service provider in the source field 148e. If the event was recorded by a CAD system and imported to the event reporting program 48, "CAD," is identified as the source of the post event record 148. Similarly, if the event was imported from an external device, such as a LIFEPAK® 12 defibrillator manufactured by Physio-Control Manufacturing Corporation of Redmond, Wash., the source field would identify the external device, e.g., "LP12," as the source of the post event record 148.

In addition to the event summary 130, the post-event window 128 also includes a device event button 132, a CAD event button 134, a narrative data button 136, an additional data button 138, a narrative edit button 140, a run report button 142, an export data button 143, a new case button 144 (for post processing another incident), and an exit button 146. The actions taken by the event reporting program 48 as each of these buttons are selected by the emergency service provider will now be described in more detail.

Figure 8B:
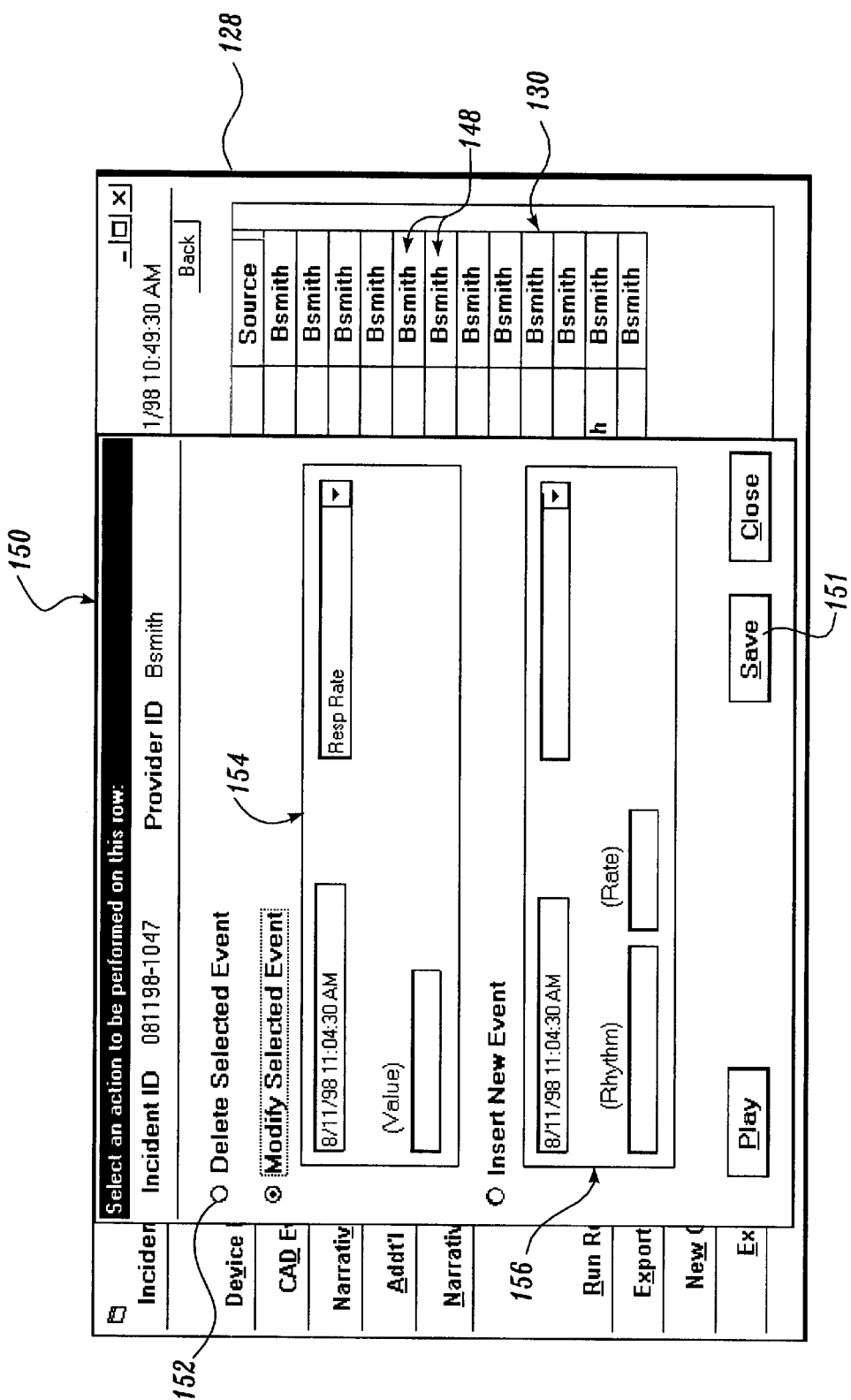

Returning to FIG. 7, once the post-event window 128 has been displayed by the event reporting program 48 in a block 232, the logic proceeds to a decision block 234 where it determines if the emergency service provider has elected to edit a post event record 148 by highlighting a post event record 148 in the event summary 130. If so, the emergency service provider is allowed to edit the post event record 148 in a block 236. More specifically, the event reporting program 48 generates an event edit window 150 as shown in FIG. 8B. The emergency service provider can delete the highlighted post event record 48 by selecting a delete event button 15; modify the highlighted post event record 148 by inputting the appropriate information in a modify event field 154; or insert a new post event record 148 immediately preceding the highlighted record by inputting the appropriate information in an insert new event field 156. When modifying an existing post event record, the provider may add or edit the time of the event, the descriptor for the event, and/or the detail associated with the event. The emergency service provider may then save the post event record 148 in the patient's record 46 in memory 48 by selecting the save button 151. Simultaneously, the corresponding post event record 148 is either deleted from, modified in, or added to the event summary 130.

Returning to FIG. 7, if the emergency service provider does not wish to edit a post event record 148 or selects this option and does so, the logic proceeds to a decision block 238 where it determines if the emergency service provider has opted to add Computer-Aided Dispatch, "CAD," events to the event summary 130 by selecting the CAD event button 134 as shown in FIG. 8C. CAD events are those that are registered by an external CAD system, typically the CAD system that dispatched the emergency service provider to the incident. By establishing a communications link between the hand-held computer 20 and a remote CAD computer via the hand-held computer's external interface 42, the emergency service provider can download CAD events from the remote CAD computer. Each CAD event consists of an event/time pair, which is formatted by the event reporting program as a post event record 148. The event reporting program 48 inserts the corresponding post event record 148 in the event summary 130 in chronological order as shown in FIG. 8C. For example, when the emergency 911 call for the incident being reported is received by a remote CAD computer, the remote CAD computer stores the time of the phone call and an event descriptor for the phone call, i.e., "Call 911," in its own memory. After the 911 event/time pair is downloaded (along with others) to the hand-held computer 20, it is inserted in the event summary 130 as post event record 148'. The time field 148a of the inserted post event record 148' includes the time recorded by the CAD computer for the 911 call; the event 148c includes a brief descriptor for the 911 event, i.e., "Call 911"; and the source field 148e indicates that the source of the post event record 148' is a CAD computer. It will be appreciated that whenever event/time pairs are imported from a CAD system or some other external device, the event reporting program 48 will synchronize the imported event times with the clock 36 of the hand-held computer so that imported event times are properly offset before added to the event summary 130.

Returning to FIG. 7, once the downloaded CAD event/time pairs have been incorporated into the event summary 130 as post event records 148, the logic proceeds to a decision block 242 where it determines if the emergency service provider has elected to add device events to the event summary 130 by selecting the device events button 132 as shown in FIG. 8D. More specifically, the event reporting program 48 detects whether the emergency service provider has selected the device event button 132 from the post-event window 128. If so, the logic proceeds to a block 244 where the device events are incorporated in the event summary 130. It will be appreciated that device events are similar to CAD events in that they are obtained from a remote device as an event/time pair and incorporated into the event summary 130 as post event records 148 in chronological order. Such devices may include medical electronic devices used by the emergency service provider to administer treatment to the patient during the incident, e.g., external defibrillators, non-invasive blood pressure instruments, etc., or other remote computer systems, such as a mainframe computer located at the hospital to which the patient will be delivered. By establishing a communication link with the external device via its external interface 42, the hand-held computer 20 can download event/time pairs recorded by the external device and insert them as post event records 148 in the event summary 130. For example, if the external device is a defibrillator, such as the LIFEPAK® 12 defibrillator, the defibrillator stores various event/time pairs relating to the treatment of the patient's cardiac condition. For example, a defibrillator typically stores an event/time pair including the measured heart rate for the treated patient and the time at which the heart rate was measured. When the device events button 132 is selected, the event/time pair for the measured heart rate is downloaded from the defibrillator to the hand-held computer 20 and inserted in the event summary 130 as a post event record 148". Accordingly, event field 148a includes the time at which the heart rate was measured; the event field 148c includes the common descriptor for the event, i.e., "Heart Rate," measured by the defibrillator; the detail entry field 148d includes the measured heart rate, i.e., 92; and the source field 148e indicates that the source of the post event record 148" is a LIFEPAK® 12 defibrillator.

Figure 8E:
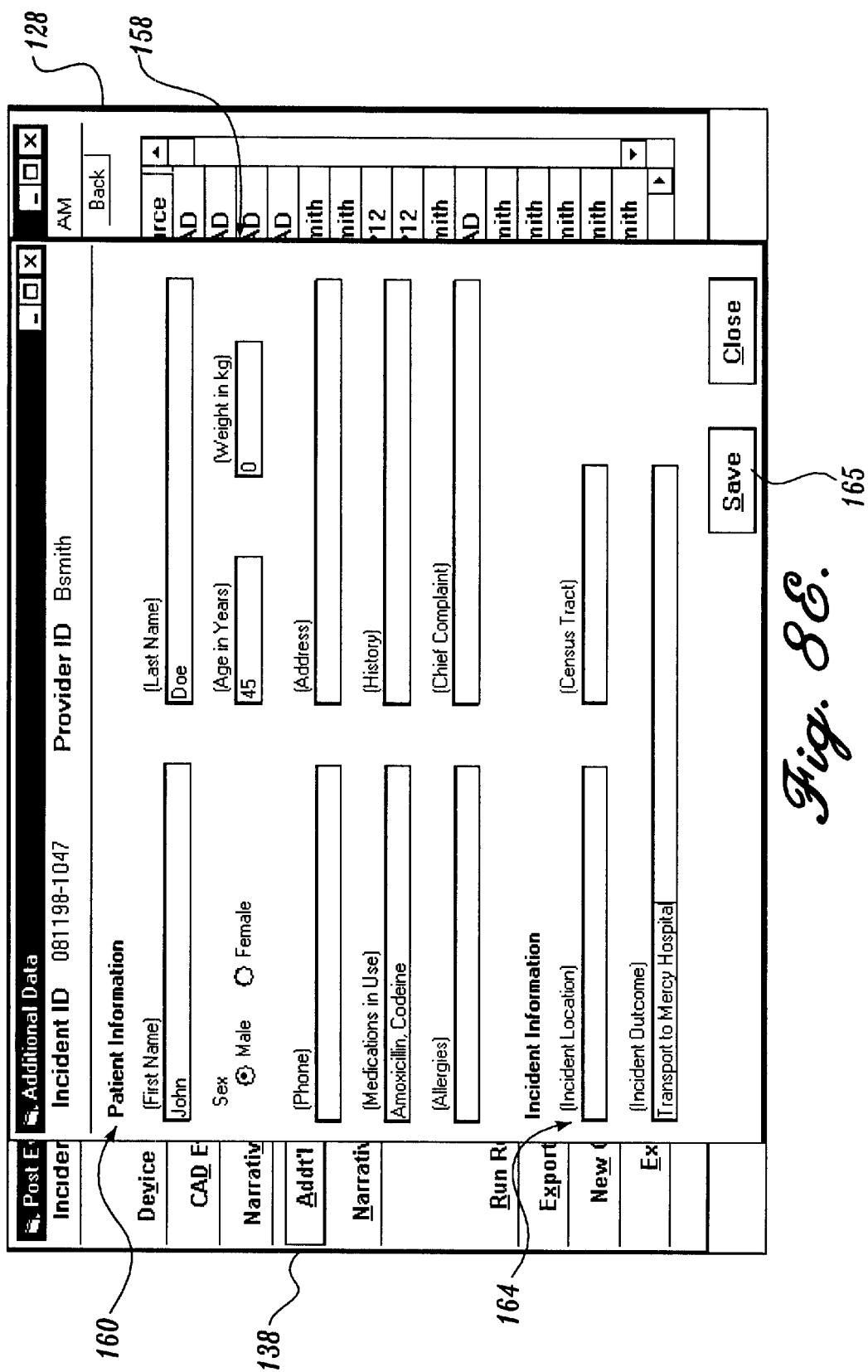

Returning to FIG. 7, once the downloaded device event/time pairs have been incorporated in the event summary 130 as post event records 148, the logic proceeds to a decision block 246 where it determines if the emergency service provider has elected to add patient data to the patient's record 46 by selecting the additional data button 138 in the post-event window 128 as shown in FIG. 8E. If so, the emergency service provider further builds the patient's record 46 in a block 248 with information obtained via a patient information window 158 generated by the event reporting program 48. The patient information window 158 includes patient information fields 160 in which the emergency service provider inserts personal information regarding the patient, such as name, age, weight, address, etc.; and incident information fields 164 in which the emergency service provider inputs information regarding the incident, such as its location and its outcome. It will be appreciated that the provider may input information in the patient information fields 160 and the incident information fields 160 using the keyboard 30 or the by speaking via the speaker/microphone 24. The newly added patient information is stored in the patient's record 46 in memory when the emergency service provider selects a save button 165 in the patient information window 158.

Once the new information has been stored in the patient's record 46, the logic returns to a decision block 250 in FIG. 7 where it determines if the emergency service provider has elected to edit the narrative previously recorded by him or her during the incident by selecting the narrative edit button 140 in the post-event window 128. If so, the emergency service provider is allowed to modify the narrative text in a block 256. More specifically, the event reporting program 48 produces a narrative story window 96 as shown previously n FIG. 6J, which includes the text of the previously recorded narrative. Accordingly, the emergency service provider may edit the text narrative using the keyboard 30 or alternatively, by voice prompting via the speaker/microphone 24.

Once the emergency service provider has modified the text of the narrative as desired, the logic returns in FIG. 7 to a decision block 254 where it determines if the emergency service provider has elected to add certain pieces of information from the narrative to the patient's record 46 by selecting the narrative data button 136 in the post-event window 128. If so, the event reporting program 48 runs a narrative parsing routine shown in more detail in FIG. 9 to identify desirable pieces of information from the narrative and add them to the patient's record 46.

Figure 9:
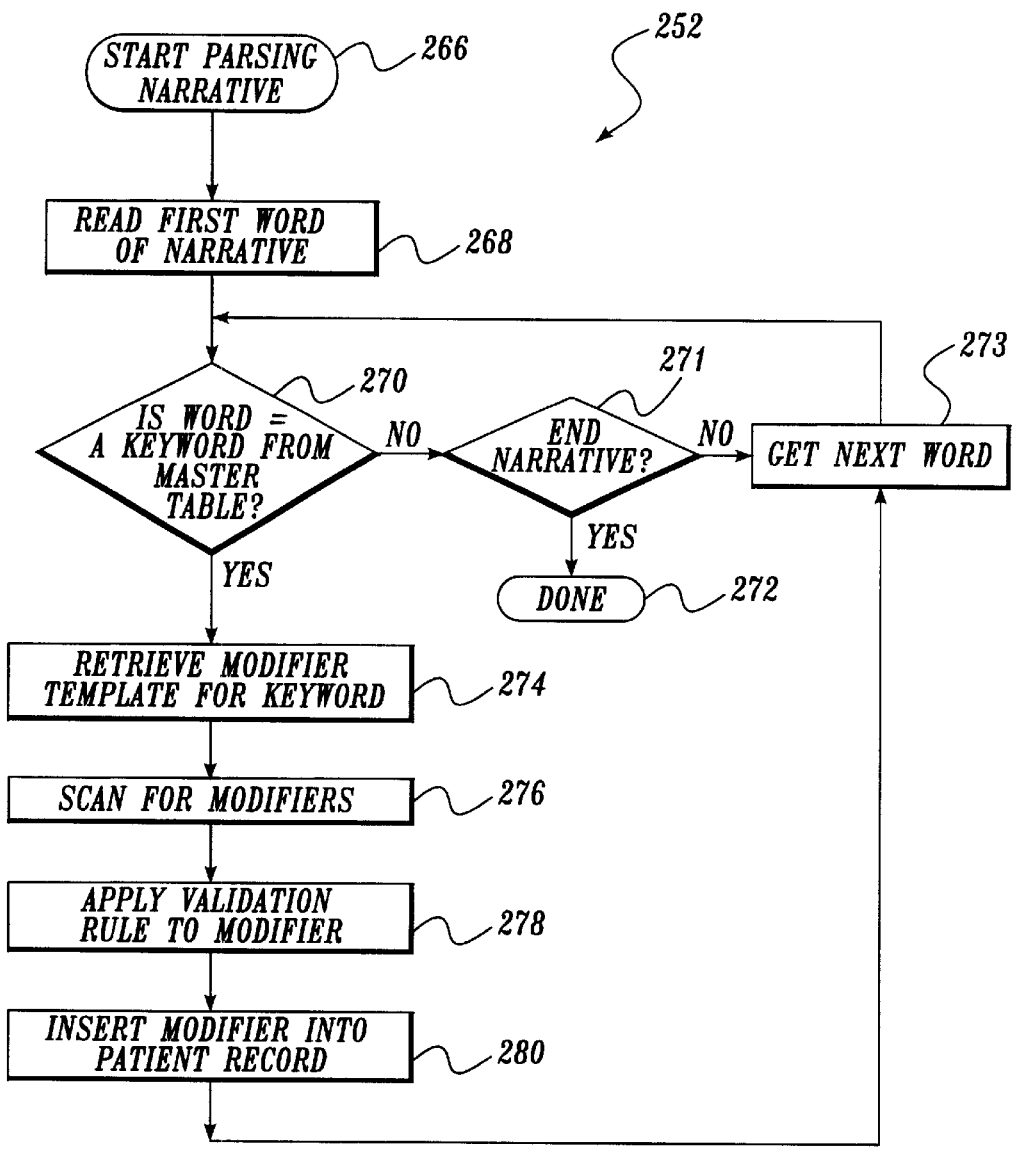
FIG. 9 is a flowchart illustrating the logic used to parse a clinical narrative previously recorded by the emergency provider for certain pertinent information.

The narrative parsing routine depicted in FIG. 9 examines the text of the narrative previously recorded and perhaps edited by the emergency service provider for pieces of data that are commonly expected to be recorded during an emergency incident, such as the age and/or sex of a patient, common symptoms for a patient, blood pressure of a patient, etc. By reviewing the text of the narrative for such information and automatically adding the information to the patient's record 46, the emergency service provider eliminates the extra task of inputting such information into the patient's records 46 manually.

Returning to FIG. 7, the narrative parsing routine begins in FIG. 9 in a block 266 and proceeds to a block 268 in which the first word of the narrative text is read. In a decision block 270, the routine determines if the read word is equal to a narrative keyword stored in a predefined list of narrative keywords found in the master tables 50. A keyword for purposes of the present invention is a word or term that is commonly expected to appear in a clinical narrative, e.g., "years(s)," "male," "female," "pressure," etc. If the first word read from the narrative is not equal to one of the keywords in the predefined list, the logic proceeds to a decision block 271 in which it determines if the end of the narrative has been reached, i.e., if the last word of the narrative has been read. If so, the narrative edit routine ends in a block 272. Otherwise, the next word in the narrative text is obtained in a block 273 and decision block 270 is repeated.

If the word obtained from the narrative is equal to one of the keywords stored in the list of keywords, a modifier template for the keyword is retrieved from the master tables 50 in a block 274. Each keyword in the list of keywords has a corresponding modifier template stored in the master tables 50 which identifies a typical pattern in which a desired word, term, or number, i.e., "modifier," is expected to appear in the text in association with the keyword. For example, if the keyword obtained from the narrative is "year(s)," the common term or modifier expected to appear with the keyword is an age for the patient. Consequently, the modifier template for the keyword identifies the following pattern for the modifier and keyword:

$$xw/5\ year(s)$$

or $$year(s)w/5x$$

wherein the modifier, i.e., the age of the patient denoted the by variable "x," is expected to appear within the five words preceding the keyword "year(s)" or within five words following the keyword "year(s)."

Once the modifier template for the key word has been retrieved in a block 274, the narrative text is scanned for the appropriate modifier that matches the modifier template in a block 276. Using the above example, the narrative text is scanned for the variable "x," i.e., age, falling within the five words preceding or following the word "year(s)." Once the modifier matching the modifier template is located, a validation rule is applied to the modifier in a block 278 to ensure that the modifier actually constitutes a desired or valid piece of information to be inserted in the patient's record 46. Again, using the example above, if the keyword obtained from the text of the narrative is "years(s)," the located modifier, i.e., the age of the patient, is validated against a rule requiring that the age be less than a maximum age permitted, e.g., 110. Yet other validation rules may require that a located blood pressure modifier, e.g., 110/60, be less than a maximum systolic pressure and greater than a minimum diastolic pressure, or that a located sex modifier of a patient be either male or female. Once validated, the modifier is inserted into the patient's record 46 in memory in a block 280. Those of ordinary skill in the art will recognize that modifier templates and validation rules of virtually any type or nature may be implemented by the event reporting program 48.

Figure 8F:
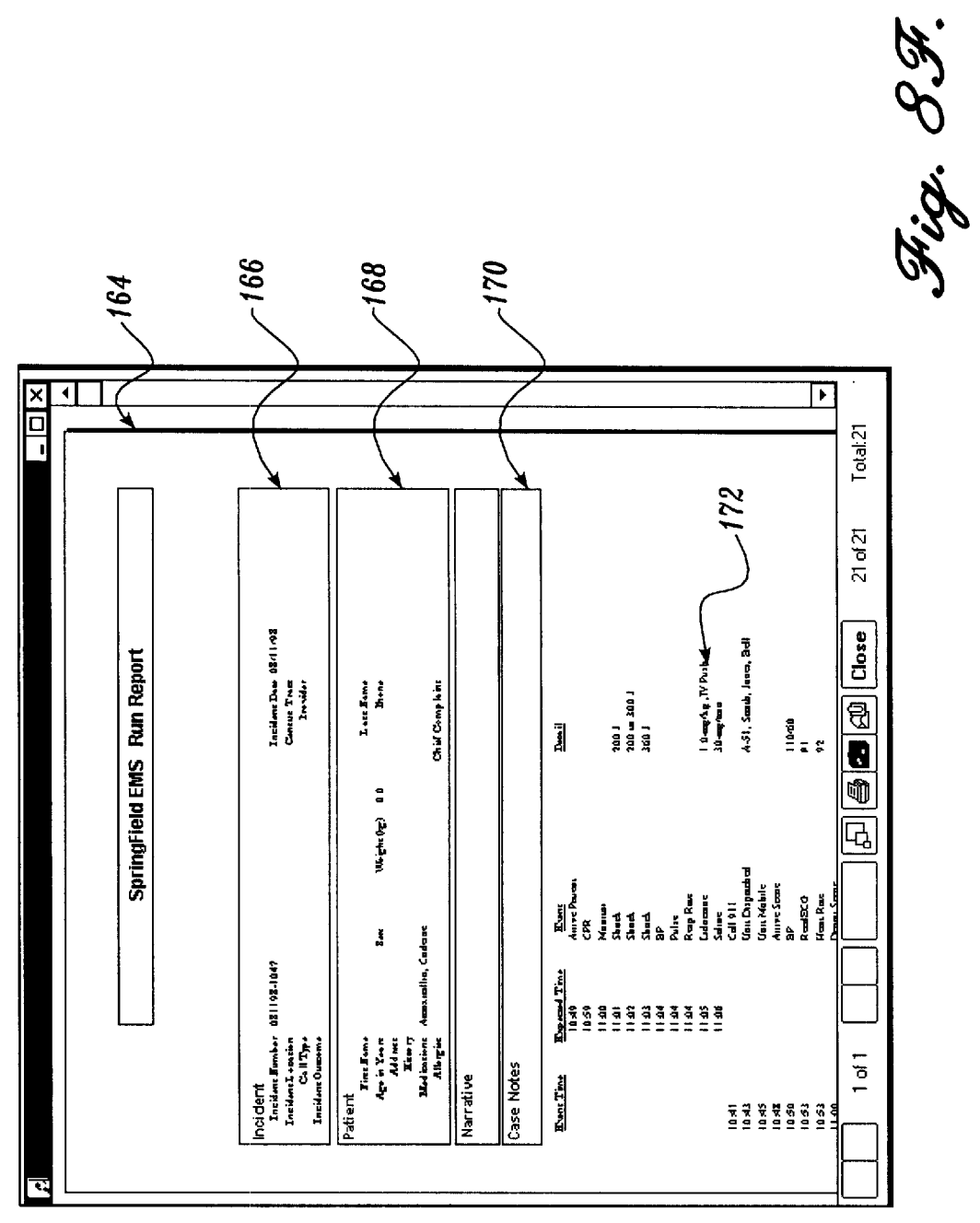

Returning to FIG. 7, once the appropriate narrative data has been parsed and added to the record 46 for the patient, the logic proceeds to a decision block 258 where it determines if the emergency service provider has elected to run a complete report of the incident by selecting the run report button 142 in the post-event window 128. If so, a full run report as shown in FIG. 8F will be generated on the display 32 of the hand-held computer from the information stored in the patient's record. It will be appreciated that the run report may also be printed, if desired. The full run report 164 includes an incident field 166 which identifies the incident by identification number, location, etc., as stored in the patient record 46 for the treated patient; a patient field 168 which includes the personal and background information stored in the patient record 46; and a narrative field 170 which includes the narrative previously edited and recorded by the emergency service provider. Finally, the run report 164 includes a complete event summary 172 that shows each of the event records 68 recorded by the emergency service provider and any remote devices or CAD systems.

After the full run report 64 has been displayed, the logic returns to a decision block 260 in FIG. 7 where it determines if the emergency service provider has elected to export data recorded by the event reporting program 48 to an external destination by selecting the export data button 143 in the post-event window 128. If so, the hand-held computer 20 transfers the patient records 46 stored in memory 44 to another device via its external interface 42 in a block 261.

In the alternative, the hand-held computer 20 stores patient records 46 to a portable storage medium, such as a diskette, for physical transfer to another device.

After export, the logic proceeds in FIG. 7 to a decision block 262 where it determines if an exit signal has been received. More specifically, the logic determines if the emergency service provider has selected the exit button 146 in the post-event window 128. If so, the event reporting program ends in a block 264. If not, the emergency service provider can continue post-processing of the incident by selecting any of the available post-processing options and repeating blocks 234 through 262.

While the preferred embodiment of the invention has been illustrated and described, it will be appreciated that various changes can be made therein without departing from the spirit and scope of the invention. For example, although the event reporting program 48 of the present invention described herein is used by an emergency service provider in the context of medical treatment of a patient during an emergency incident, the present invention may be just as easily used in a multitude of other contexts. For example, the invention could be used by a police officer in the context of an emergency criminal incident. In this case, the events recorded and tools initiated would relate to the arrest of a suspect, rather than medical treatment of a patient. In accordance with yet other aspects of the invention, a separate log may be kept of all recorded, modified and deleted events for use in auditing the final event summary 172 for inaccuracies. Finally, in yet other embodiments of the present invention, a digital audio recorder may be used to record all of the emergency service provider's verbal inputs during the entire incident along with their associated time stamps as an audio event log. The audio event log could then be compiled and transcribed into an event summary and run report following completion of the incident.

The embodiments of the invention in which an exclusive property or privilege is claimed are defined as follows:

1. A method for recording an emergency incident, wherein the emergency incident comprises a collection of events, the method comprising:
    (a) identifying the incident;
    (b) recording an event/time pair for each event that occurs during the identified incident, wherein the event/time pair identifies the event and a time at which the event occurred during the incident, wherein the act of recording records a narrative describing the incident;
    (c) parsing the recorded narrative for at least one expected modifier, wherein parsing the recorded narrative comprises:
        (i) identifying at least one keyword in the narrative which indicates the presence of the expected modifier in the narrative;
        (ii) identifying a modifier template associated with the keyword which identifies a narrative pattern in which the expected modifier and keyword typically appear; and
        (iii) scanning the narrative to locate a modifier which matches the modifier template.

2. The method of claim 1, wherein parsing the recorded narrative further comprises comparing the located modifier with a validation rule to ensure that the located modifier is valid.

3. The method of claim 1, further comprising:
    for at least one expected event/time pair, issuing an alarm indicating the occurrence of an expected event when the time at which the event is expected to occur passes.

4. The method of claim 1, further comprising, in addition to changing event/time pair records based on actions that occur during the handling of the identified emergency incident, recording information that further describes the emergency incident.

5. The method of claim 1, further comprising generating a report containing the recorded event/time pairs.

6. The method of claim 1, further comprising exporting the recorded event/time pairs to an external destination.

7. A computer-readable medium having computer executable components for recording and reporting an emergency incident, wherein the incident comprises a plurality of events associated with treatment of a patient during the incident, the computer-readable medium having computer-executable components comprising:
    (a) an event recording component for recording events as they occur during the incident, wherein the event recording component records events by enabling a user to input a plurality of event records, wherein each event record identifies an event which occurred during the incident and a time at which the event occurred, wherein the event recording component enables the user to input a narrative story describing the incident; and
    (b) a post-processing component for further processing the events recorded by the event recording component, wherein the post-processing component processes the narrative story input by the user by parsing the narrative story for predefined information, wherein the post-processing component parses the narrative story by:
        (i) identifying at least one keyword in the narrative story which indicates the presence of the expected modifier in the narrative;
        (ii) identifying a modifier template associated with the keyword which identifies a narrative pattern in which the expected modifier and keyword typically appear; and
        (iii) scanning the narrative story to locate a modifier which matches the modifier template.

8. The computer-readable medium of claim 7, wherein parsing the recorded narrative story further comprises comparing the located modifier with a validation rule to ensure that the located modifier is valid.

9. The computer-readable medium of claim 7, wherein the event recording component further records events by enabling the user to input a predefined treatment protocol for the patient, wherein the predefined treatment protocol comprises a plurality of predefined event records and wherein each predefined event record identifies an event which is expected to occur during the incident and a time at which the event is expected to occur during the incident.

10. The computer-readable medium of claim 9, wherein the event recording component enables the user to modify at least one selected event record.

11. The computer readable medium of claim 7, wherein the event recording component enables the user to input event records verbally.

12. The computer-readable medium of claim 7, wherein the event recording component has at least one computer-executable subcomponent for providing information in addition to the plurality of event records recorded by the event recording component.

13. The computer-readable medium of claim 12, wherein said at least one computer-executable subcomponent for providing information is an address book subcomponent for providing address information to the user.

14. The computer-readable medium of claim 12, wherein said at least one computer-executable subcomponent for providing information is a medication identification subcomponent for enabling the user to record medication information regarding the patient.

15. The computer-readable medium of claim 12, wherein said at least one computer-executable subcomponent for providing information is a stop watch subcomponent for timing the duration of an action taken by the user.

16. The computer-readable medium of claim 12, wherein said at least one computer-executable subcomponent for providing information is a drug guideline subcomponent for providing drug information to the user.

17. The computer-readable medium of claim 12, wherein said at least one computer-executable subcomponent for providing information is a medication dosage/infusion calculating component for calculating the dosage/infusion rate of a drug to be administered by the user to the patient.

18. The computer-readable medium of claim 7, wherein the post-processing component further processes the events recorded by the event recording component by enabling the user to modify at least one selected event record previously recorded by the event recording component.

19. The computer-readable medium of claim 7, wherein the post-processing component further processes the events recorded by the event recording component by enabling the user to record at least one event record in addition to those previously recorded by the event recording component.

20. The computer-readable medium of claim 19, wherein the post-processing component enables the user to verbally record said at least one event record.

21. The computer-readable medium of claim 7, wherein the post-processing component further processes the events recorded by the event recording component by enabling the user to incorporate event records recorded by an external source, wherein each event record incorporated identifies an event recorded by the external source and a time recorded by the external source at which the event occurred.

22. The computer-readable medium of claim 7, wherein the post-processing component further processes the events recorded by the event recording component by enabling the user to record additional information regarding the incident.

23. The computer-readable medium of claim 7, wherein the post-processing component further processes the events recorded by the event recording component by exporting recorded events to external devices.

24. The computer-readable medium of claim 7, wherein the post-processing component further processes the events recorded by the event recording component by generating a run report containing all of the event recorded by the event recording component and further processed by the post-processing component.

25. An apparatus for reporting for reporting an emergency incident, wherein the incident comprises a plurality of events associated with treatment of a patient during the incident, the apparatus comprising:
   (a) a processing unit; and
   (b) a storage medium coupled to the processing unit, the storage medium containing program code executed by the processing unit for recording an event/time pair for each event as it occurs during the incident, wherein the event/time pair identifies the event and a time at which the event occurred during the incident, wherein the storage medium further contains program code executed by the processing unit for recording a narrative describing the incident, wherein the storage medium further contains program code executed by the processing unit for parsing the narrative for an expected modifier comprising a piece of desired information, wherein the narrative is parsed by:
      (i) identifying at least one keyword in the narrative which indicates the presence of the expected modifier in the narrative;
      (ii) identifying a modifier template associated with the keyword which identifies a narrative pattern in which the expected modifier and keyword typically appear; and
      (iii) scanning the narrative to locate a modifier which matches the modifier template.

26. The apparatus of claim 25, wherein parsing the recorded narrative further comprises comparing the located modifier with a validation rule to ensure that the located modifier is valid.

27. The apparatus of claim 25, further comprising a microphone coupled to the processing unit for receiving event/time pairs verbally input by a user, wherein the event/time pairs verbally input by the user are recorded by the program code stored in the storage medium and executed by the processing unit.

28. The apparatus of claim 25, further comprising a display coupled to the processing unit for displaying the recorded event/time pairs in an event summary.

29. The apparatus of claim 25, further comprising an external interface coupled to the processing unit for exporting recorded event/time pairs to an external destination.

30. The apparatus of claim 29, wherein the external interface coupled to the processing unit imports event/time pair records recorded by an external source.

31. The apparatus of claim 25, wherein the storage medium further contains program code executed by the processing unit for recording a predefined protocol of events, wherein the predefined protocol of events comprises a collection of expected event/time pairs, and wherein each expected event/time pair identifies an event that is expected to occur during the incident and a time at which the event is expected to occur during the incident.

32. The apparatus of claim 31, wherein the storage medium further contains program code executed by the processing unit for issuing an alarm indicating the occurrence of at least one expected event of the predefined protocol when the time at which the event is expected to occur passes.

33. The apparatus of claim 25, wherein the storage medium further contains program code executed by the processing unit for recording information describing the incident in addition to the event/time pairs and the narrative.

34. The apparatus of claim 33, wherein the storage medium further contains program code executed by the processing unit for generating a report containing the recorded event/time pairs, information and narrative.

35. The apparatus of claim 25, wherein the storage medium further contains program code executed by the processing unit for modifying previously recorded event/time pairs.

36. The apparatus of claim 25, wherein the storage medium further contains program code executed by the processing unit for providing address information to a user.

37. The apparatus of claim 25, wherein the storage medium further contains program code executed by the processing unit for providing medication information to a user.

38. The apparatus of claim 25, wherein the storage medium further contains program code executed by the processing unit for providing a stop watch to a user.

39. The apparatus of claim 25, wherein the storage medium further contains program code executed by the processing unit for providing drug guideline information to a user.

40. The apparatus of claim 25, wherein the storage medium further contains program code executed by the processing unit for calculating a dosage of medication.

* * * * *